United States Patent
Chiou et al.

(10) Patent No.: US 9,107,934 B2
(45) Date of Patent: Aug. 18, 2015

(54) MICRORNA AS A CANCER PROGRESSION PREDICTOR AND ITS USE FOR TREATING CANCER

(71) Applicant: Taipei Veterans General Hospital, Taipei (TW)

(72) Inventors: Shih-Hwa Chiou, Taipei (TW); Guang-Yuh Chiou, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 174 days.

(21) Appl. No.: 13/725,586

(22) Filed: Dec. 21, 2012

(65) Prior Publication Data
US 2013/0108691 A1 May 2, 2013

Related U.S. Application Data

(62) Division of application No. 13/074,719, filed on Mar. 29, 2011.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12N 15/63* | (2006.01) | |
| *A61K 31/7088* | (2006.01) | |
| *C12N 15/113* | (2010.01) | |

(52) U.S. Cl.
CPC .......... *A61K 31/7088* (2013.01); *C12N 15/113* (2013.01); *A01K 2267/0331* (2013.01); *C12N 2310/113* (2013.01); *C12N 2310/141* (2013.01); *C12N 2310/315* (2013.01); *C12N 2310/3231* (2013.01); *C12N 2310/346* (2013.01); *C12N 2320/31* (2013.01); *C12N 2330/10* (2013.01)

(58) Field of Classification Search
CPC ................ C12N 2310/141; C12N 2330/10; C12N 15/113
See application file for complete search history.

(56) References Cited

U.S. PATENT DOCUMENTS

| | | | |
|---|---|---|---|
| 7,670,840 B2 | 3/2010 | Croce et al. | |
| 7,741,306 B2 | 6/2010 | Slack et al. | |
| 7,745,134 B2 | 6/2010 | Chen et al. | |
| 7,812,003 B2 | 10/2010 | Safe et al. | |
| 8,404,437 B2 * | 3/2013 | Chiou et al. | 435/6.14 |

FOREIGN PATENT DOCUMENTS

WO    WO 2008142567    11/2008

OTHER PUBLICATIONS

Garzon et al., 2009, Annu. Rev. Med., vol. 60, p. 167-179.
Ferretti et al., 2008, The EMBO Journal, vol. 27, No. 19, p. 2616-2627.
Bissels et al., 2011, Stem Cells, vol. 29, p. 847-857.
Joo et al., 2008, Laboratory Investigation, vol. 88, p. 808-815.
Huang et al., 2009, EMBO Reports, vol. 10, No. 2, p. 180-185.
Malzkorn et al., 2010, Brain Pathology, vol. 20, p. 539-550.
Fang et al., 2011, BMC Genomics, vol.12, No. 11, p. 1-17.
Gangemi et al., 2009, Stem Cells, vol. 27, No. 1, p. 40-48.
Chiou et al., 2006, Childs Nerv Syst, vol. 22, p. 475-480.

* cited by examiner

*Primary Examiner* — Amy Bowman
(74) *Attorney, Agent, or Firm* — Volpe and Koenig, P.C.

(57) ABSTRACT

The present invention is based on the findings that a novel function for miR142-3p in the regulation of Sox2, adenylyl cyclase 9 (AC9), and CD133 expressions, and consequently the overall stemness of recurrent GBM cells as well as CSCs, and that miR142-3p modulated tumor-initiating properties in recurrent GBM. The present invention consequently supports the development of novel miRNA-based strategies for brain tumor treatment.

9 Claims, 17 Drawing Sheets
(10 of 17 Drawing Sheet(s) Filed in Color)

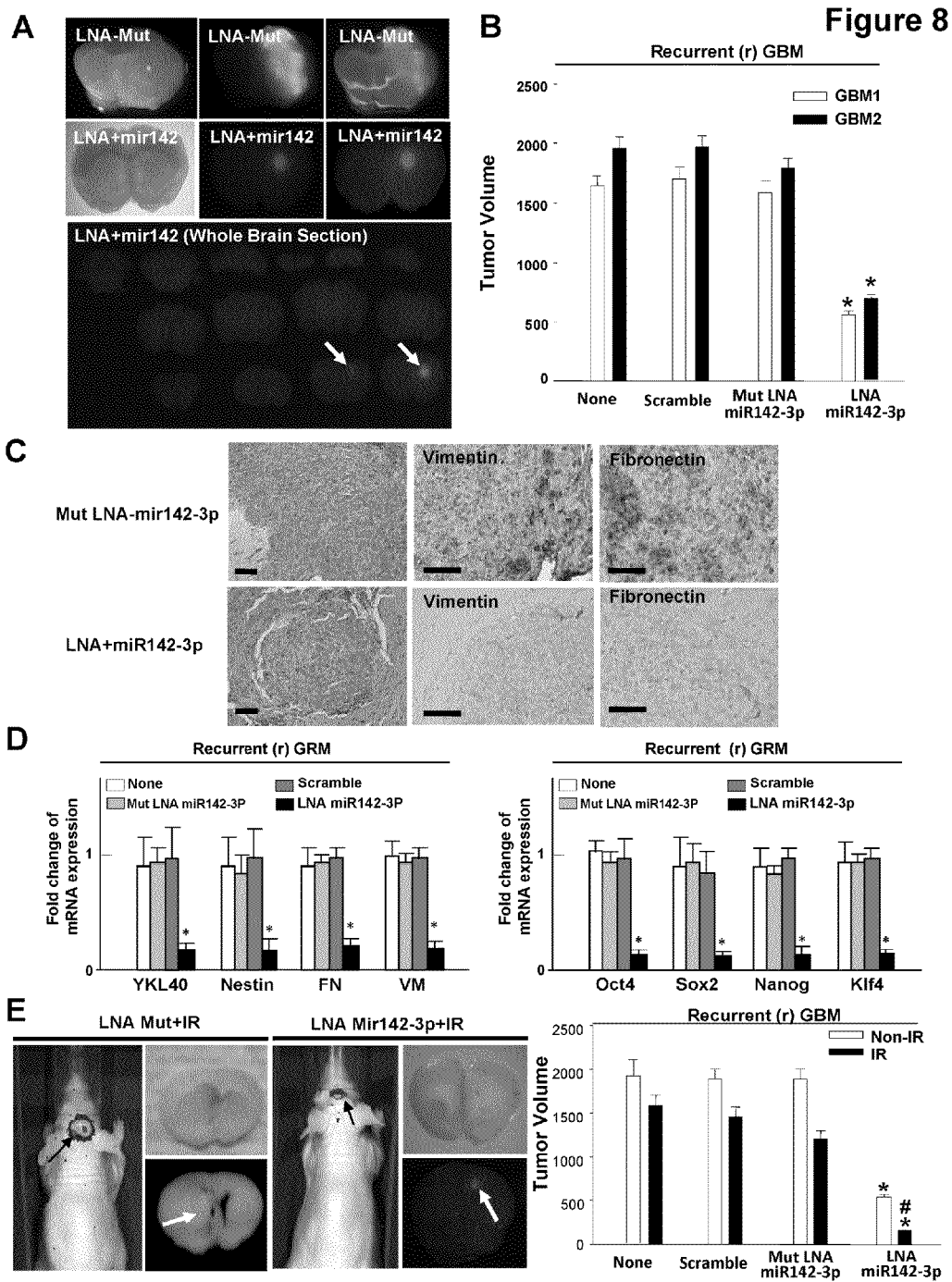

Evaluation of tumor-initiating ability and tumor formation in Sponge-Mir142-3p-GBM cells in NOD-SCID mice

| Patients | Injected Cells Numbers | Parental | pLV-Scramble | pLV-Mir142-Sponge | Mir142-Sponge + shRNA | Mir142-Sponge + sh-AC9/sh-Sox2 | Mir142-Sponge + sh-AC9/Sox2/CD133 |
|---|---|---|---|---|---|---|---|
| No.9 | 10,000 | 2/3 | 1/3 | 3/3 | 3/3 | 3/3 | 3/3 |
|  | 1,000 | 0/3 | 0/3 | 3/3 | 2/3 | 0/3 | 1/3 |
|  | 100 | 0/3 | 0/3 | 1/3 | 1/3 | 0/3 | 0/3 |
|  | 50 | 0/3 | 0/2 | 1/3 | 0/3 | 0/2 | 0/3 |
| No.10 | 10,000 | 1/3 | 0/3 | 2/3 | 3/3 | 1/3 | 1/3 |
|  | 1,000 | 0/3 | 0/3 | 3/3 | 3/3 | 0/3 | 0/3 |
|  | 100 | 0/3 | 0/3 | 2/3 | 1/3 | 0/3 | 0/3 |
|  | 50 | 0/3 | 0/3 | 1/2 | 0/3 | 0/3 | 0/3 |
| No.11 | 10,000 | 3/3 | 3/3 | 3/3 | 3/3 | 2/3 | 2/3 |
|  | 1,000 | 1/3 | 0/3 | 3/3 | 2/3 | 0/3 | 0/3 |
|  | 100 | 0/3 | 0/3 | 2/3 | 2/3 | 0/3 | 0/3 |
|  | 50 | 0/3 | 0/3 | 0/3 | 0/2 | 0/3 | 0/3 |
| No.12 | 10,000 | 1/3 | 1/3 | 3/3 | 3/3 | 1/3 | 1/3 |
|  | 1,000 | 0/3 | 0/3 | 3/3 | 3/3 | 0/3 | 0/3 |
|  | 100 | 0/3 | 0/3 | 3/3 | 2/3 | 0/3 | 0/3 |
|  | 50 | 0/2 | 0/3 | 1/3 | 1/3 | 0/2 | 0/3 |
| No.13 | 10,000 | 2/3 | 2/3 | 3/3 | 3/3 | 3/3 | 3/3 |
|  | 1,000 | 1/3 | 0/3 | 2/3 | 3/3 | 1/3 | 1/3 |
|  | 100 | 0/3 | 0/3 | 2/3 | 1/3 | 0/3 | 0/3 |
|  | 50 | 0/3 | 0/2 | 2/2 | 0/3 | 0/3 | 0/2 |

Mir142-Sponge + ShRNA: pLV-Mir142-Sponge with shRNA vector
Mir142-Sponge + Sh-AC9/SH-Sox2: pLV-Mir142-Sponge combined with shRNA-AC9 and shRNA-Sox2

Fig. 15

MICRORNA AS A CANCER PROGRESSION PREDICTOR AND ITS USE FOR TREATING CANCER

CROSS REFERENCE TO RELATED APPLICATIONS

This application is a divisional application of U.S. patent application Ser. No. 13/074,719, filed Mar. 29, 2011, which is incorporated by reference as if fully set forth.

The sequence listing electronically filed with this application, titled "Sequence Listing," having a file size of 9,767 bytes, and created on Dec. 21, 2012 is incorporated herein by reference as if fully set forth.

FIELD OF THE INVENTION

The preset invention relates to microRNA as a cancer progression predictor and its use for treating cancer.

BACKGROUND OF THE INVENTION

Glioblastoma multiforme (GBM), grade IV glioma, is the most malignant primary brain tumor, with a very poor prognosis (Stupp et al., 2005); the median survival is around 12 months, despite combined multimodal therapy (Dehdashti et al., 2006; Stupp et al., 2007; Stupp et al., 2005). To improve patient survival, the mechanisms of GBM's tumorigenesis need to be elucidated. Some studies have suggested that subsets of cancer stem cells (CSC) are key contributors to radioresistance and responsible for tumor progression as well as recurrence after conventional therapy (Bao et al., 2006). However, there is lack of suitable markers for isolating the crucial subset of tumor cells that is capable of reforming new tumors in vivo and accounts for tumor relapse in malignant glioma, according to CSC hypothesis of tumorigenesis (Chen et al., 2010).

MicroRNAs (miRNAs)—highly conserved small RNA molecules that regulate gene expression—can act as cancer signatures, oncogenes or tumor suppressors (Croce, 2009). MiRNAs appear to target oncogenes, cell cycle regulators and transcription factors, and regulate brain tumor progression (Gillies and Lorimer, 2007). In brain tumors, multiple miR-NAs, including miR7, miR21, miR26a, miR124, miR137, miR184, and miRNA 221/222 have been implicated in GBM pathogenesis (Chan et al., 2005; Chen et al., 2008; Diehn et al., 2009; Huse et al., 2009; Kefas et al., 2008; Li et al., 2009; Malzkorn et al., 2009). Several miRNAs appear to be prognostic markers, such as miR10b and miR26a in high-grade glioma (Huse et al., 2009; Sasayama et al., 2009). MiRNAs are involved in many aspects of brain tumor progression, including glioma malignant progression. MiR125b, miR326, and miR324-5p—signature miRNAs in cerebellar neuronal progenitors and tumors—can help predict prognosis and patient outcome (Ferretti et al., 2008). Further, miR34 overexpression impairs the self-renewal properties of brain tumor and pancreatic cancer stem cells (CSCs) (Ji et al., 2009b). Recently, miR145 was found to modulate embryonic stem cell differentiation; this single miRNA simultaneously regulated multiple stemness genes, including KLF4, Oct4, and Sox2 (Xu et al., 2009). However, whether there is such a role for miRNAs in GBM relapse and secondary GBM that is mediated by regulation of stemness, tumor-initiating capability or mesenchymal transformation is unclear.

Mir142 was first reported to regulate hematopoiesis and T cell development (Chen et al., 2004). MiR142-3p expression is controlled by LMO2 binding to the putative promoter region of the miR142 gene (Yuan et al., 2008). The miR142 gene resides at the junction of the t(8;17) translocation, which appears to be associated with indolent lymphoma progression to aggressive B-cell leukemia due to strong upregulation of c-Myc (Gauwerky et al., 1989). Qian et al. (2008) found miR142-3p and miR142-5p upregulation in bronchioalveolar stem cells (BASCs) in mouse lung; aberrant miR142 expression could be involved in converting BASCs into lung cancer stem cells. Recently, Sun et al. (Sun et al., 2010) showed that miR-142 attenuates hematopoietic cell proliferation regulated by the miR-223-CEBP-β-LMO2 axis. CSCs isolated from glioma or GBM had elevated expression of stemness genes such as Sox2 (Gangemi et al., 2009). Sox2, a high-mobility-group DNA binding protein, is a critical marker of neural stem cells and has a key role in maintaining their undifferentiated state. Likewise, Sox2 expression has been proposed to be a signature of glioma and medulloblastoma and maintains CSC stemness (Decarvalho et al.; Sutter et al.). Importantly, gliosarcoma stem cells have high Sox2 expression, and Sox-2 knockdown further suppressed tumorigenicity and stemness in glioma CSCs (Decarvalho et al.).

BRIEF SUMMARY OF THE INVENTION

The present invention is based on the findings that a novel function for miR142-3p in the regulation of Sox2, adenylyl cyclase 9 (AC9), and CD133 expressions, and consequently the overall stemness of recurrent GBM cells as well as CSCs, and that miR142-3p modulated tumor-initiating properties in recurrent GBM. The present invention consequently supports the development of novel miRNA-based strategies for brain tumor treatment.

Accordingly, in one aspect, the present invention provides a method for suppressing the expression of a target gene in a cell, comprising introducing miR142-3p into the cell, wherein the target gene encoding CD133, Sox2, or AC9.

In one embodiment, the miR142-3p directly connects to 3' side untranslated regions (3' UTR) of the mRNA of the target gene.

In another embodiment, the cell is a recurrent glioblastoma multiforme (GBM) cell.

In another aspect, the present invention provides a method for diagnosing or predicting whether a subject has, or is at risk for developing recurrent glioblastoma multiforme after treatment, comprising:

(a) measuring the level of miR142-3p in a control sample from the subject with primary GBM;

(b) measuring the level of miR142-3p in a test sample from the same subject after treatment; and (c) comparing the level of miR142-3p in the test sample of step (b) to the level of miR142-3p in the control sample of step (a), wherein the level of miR142-3p in the test sample of step (b) lower than the level of miR142-3p in the control sample of step (a) by indicates that the subject has, or is at risk for developing recurrent glioblastoma multiforme after treatment.

In one embodiment, in the above method, the subject has been subjected to surgical treatment, chemical treatment, radio therapy, or a combination thereof.

In another embodiment, in the above method, the subject is a patient having grade I, II, III, or IV glioma.

In still another aspect, the present invention provides a method for treating glioblastoma multiforme in a subject, comprising administering a therapeutically effective amount of miR142-3p to the subject in need thereof. The miR142-3p may be administered into a tumor locus by a stereotaxic apparatus. The glioblastoma multiforme may be recurrent glioblastoma multiforme. And the miR142-3p may be a modified microRNA with LNA- and phosphorothioate-modified backbone.

In still another aspect, the present invention provides a method for producing a glioblastoma multiforme animal model, comprising:
(a) preparing a primary glioma cell;
(b) introducing a miR142-3p antisense oligonucleotide into the primary glioma cell to obtain a miR142-3p depleted cells;
(c) transplanting the miR142-3p depleted cells to an animal to obtain the animal suffering from glioblastoma multiforme.

In still another aspect, the present invention provides a method for increasing the sensitivity of a glioblastoma multiforme cell to radiotherapy comprising administering a therapeutically effective amount of miR142-3p to the glioblastoma multiforme cell.

The various embodiments of the present invention are described in details below. Other characteristics of the present invention will be clearly presented by the following detailed descriptions and drawings about the various embodiments and claims.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

For the purpose of illustrating the invention, there are shown in the drawings embodiments which are presently preferred. It should be understood, however, that the invention is not limited to the preferred embodiments shown.

In the drawings:

FIGS. 1A-G show the miR142-3p was used as a reverse predictor of recurrent GBM signature.

FIGS. 2A-E show the phenomenon of low miR142-3p and high Sox2 and AC9 expression levels that were prediction marker of recurrent GBM and low overall survival rate.

FIGS. 3A-F show that MiR-142-3p directly targeted Sox2, ADCY9, and CD133 3' UTRs regions in GBM cells.

FIGS. 4A-G show that MiR142-3p attenuated the self-renewal and tumorigenicity of GBM cells.

FIGS. 5A-H show that MiR142-3p SPOMGE restored the stemness and tumor-initiating ability in primary GBM cells.

FIGS. 6A-G show that MiR142-3p and Sox2/AC9 expression regulated the mesenchymal transformation and proneuronal transition in GBM.

FIGS. 7A-G show that MiR142-3p, Sox2 and AC9 modulated the tumor-initiating ability and radiosensitivity in GBM cells.

FIGS. 8A-E show that MiR142-3p modulated tumorigenicity of recurrent GBM cells and radiation sensitivities.

Figure 9A:
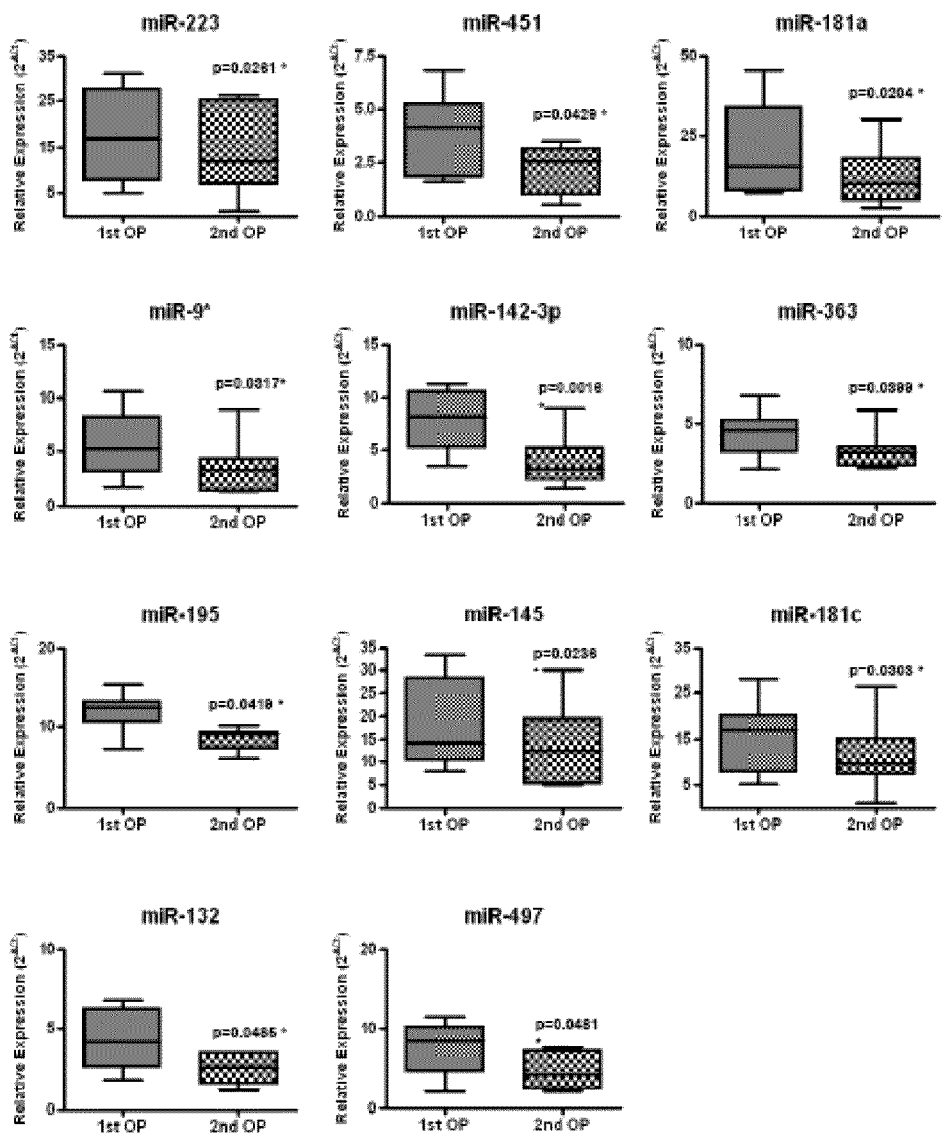
Figure 9B:
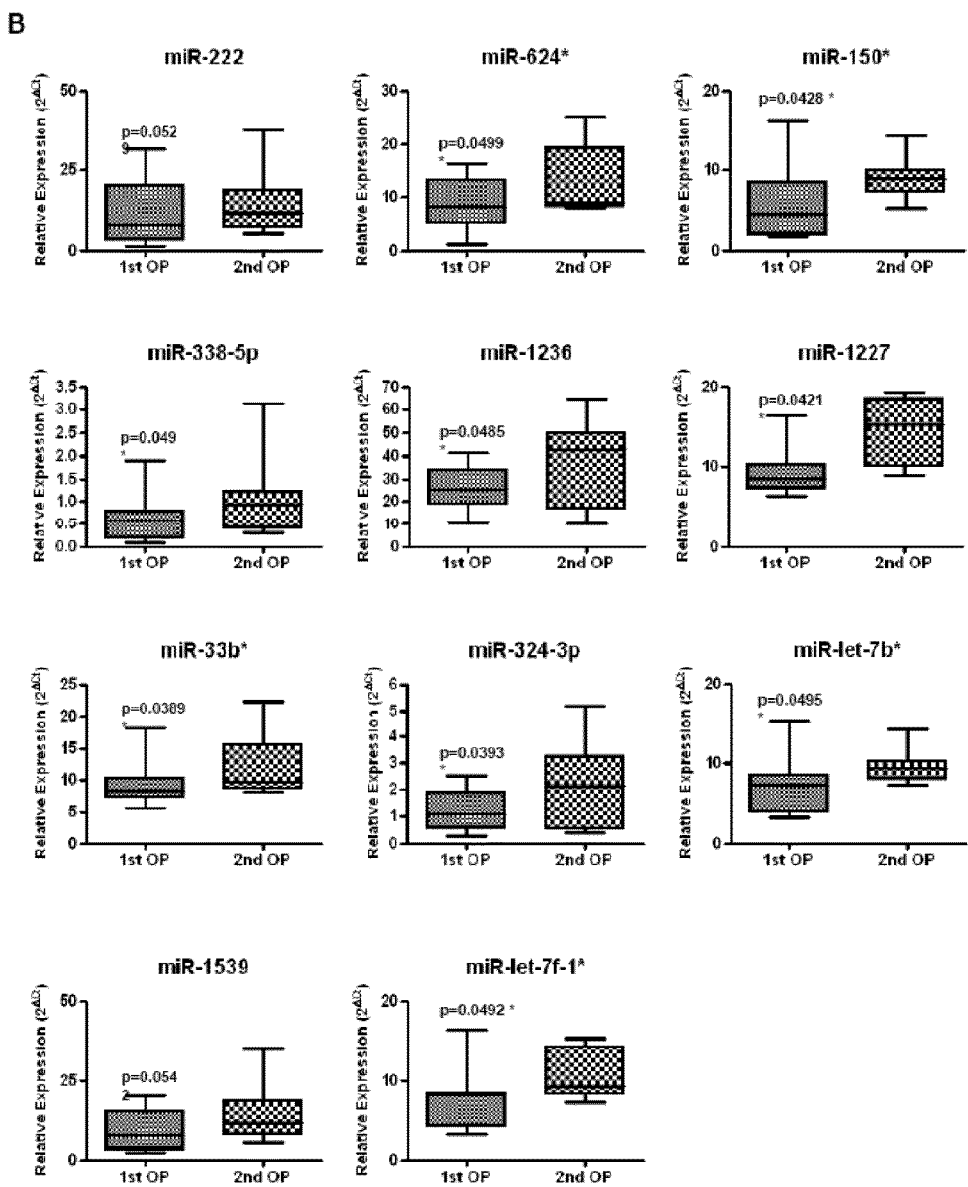

FIGS. 9A-B show the quantitative RT-PCR analysis of the expression levels of 22 miRNAs in primary (N=70) and recurrent (N=30) GBM patients, including the reduced expression of miR223, miR451, miR181a, miR9, miR142-3p, miR195, miR145, miR181c, miR132, and miR497 in recurrent GBM, among which the p-value of miR142-3p (p=0.0016) was the most significant between the primary (first operation) and recurrent (second operation) of GBMs (the data shown here were the mean±SD of 3 independent experiments).

FIGS. 10A-C show that the wild-type (WT) or mutated (mut) 3'UTR reporters of Sox2(A), AC9 (B), and CD133 (C) were co-transfected with or without antisense and SPOMGE against miR142-3p, wherein the luciferase activity of each reporter plasmid was measured and showed that either mutated 3'UTR, antisense-miR142-3p, or SPOMGE-miR142-3p abolished miR142-3p inhibition of Sox2, AC9, and CD133 3'UTR (*p<0.05).

FIGS. 11A-F show that Investigation of tumorigenicity of Sox2 and AC9 in GBM cells. (A, B, C, D) pGBM/pLV, pGMB/Sox2, pGBM/AC9, rGBM/shScr, rGBM/shSox2, and rGBM/shAC9 cell lines were established and subjected to soft agar colony formation (A, B) and sphere formation (C,D) assays; (E) the overexressed Sox2 or AC9 increased anchorage independence and self-renewal of pGBM, whereas knock-down of Sox2 or AC9 decreased both ability in rGBM; the rGBM/miR142-3p cells were used to further generate rGBM/miR142-3p/shSox2+shAC9 and rGBM/miR142-3p/Sox2+AC9 cell lines; and the protein levels of Sox2 and AC9 were assessed by Western blot; (F) the size of xenograft tumors derived from mice transplanted with the cells indicated was measured. Co-overexpression of Sox2/AC9 increased the size of rGBM/miR142-3p tumor (*p<0.05).

FIGS. 12A-F show the investigation of tumorigenicity of CD133 in GBM cells: (A) pGBM/CD133 cell lines were generated from cells derived from patient GBM1 and GBM2; and the protein expression of CD133 in each cell lines was evaluated by Western blot; (B, C, D) pGBM/CD133, rGBM/shCD133 and their control cells were subjected to soft agar colony formation (B), sphere formation (C), and TransWell invation/migration (D) assays; the presence or absence of CD133 had little effect on the anchorage independence, self-renewal, and invasion/migration ability of both pGBM cell lines; (E) the evaluation of tumor growth and volume in transplanted graft of rGBM/shScr and rGBM/shCD133 in the brain striatum of NOD-SCID mice. No significant difference was observed; and (F) the tumor volume from NOD-SCID mice transplanted with the cells indicated were measured 28 days after the transplantation; wherein no significant difference were observed between rGBM/shScr and rGBM/shCD133 tumors, as well as between pGBM/pLV and pGBM/CD133 tumors.

FIGS. 13A-C show the expressions of miR142-3p in cancer stem-like cells isolated from seven GBM patients: (A) Left panel: Microscopic images of spheroids of two independent GBM cell lines (GBM1 and GBM2), wherein the right panel: the reduced expressions of miR142-3p in spheroid-forming GBMs in seven patients; (B) the left panel: the endogenous expression of miR142-3p was detected by FISH (fluorescent in situ hybridization; green color: positive for miR142-3p expression; GBM1). Right panel: the result showed that expressions of miR142-3p was down-regulated in CD133-positive (CD133$^+$) GBM cells as compared to CD133$^-$ GBM cells in seven patient pairs; (C) the left panel: Side populations of GBM cells were separated and isolated by cell sorter (GBM1). Right panel: Reduced miR-142-3p expressions in side population (SP)-positive GBM cells in seven patients. *p<0.05.

FIGS. 14A-B show the microarray and bioinformatic analysis of the transcriptome profilings in embryonic stem cells (ESCs) and GBMs: (A) the bioinformatics analysis on transcriptome signature between ESCs, rGBM, rGBM with miR142-3p, pGBM, and pGBM with miR142-3p SPONGE.

The right panel listed the genes commonly up-expression in ESCs and rGBMs; and the genes in red, up-expression; in blue, down-expression; (B) the multidimensional scaling analysis illustrated the average lineage transcriptome distances between ESCs, rGBM, rGBM with miR142-3p, pGBM, and pGBM with miR142-3p SPONGE.

FIG. 15 shows that the evaluation of the tumor initiating ability of knock-down of miR142-3p with SPONGE method in pGBM cells isolated from five patients; and the respective amounts of 50, 100, 1000, and 10000 cells were orthotopically injected, as indicated, into the brain striatum of SCID mice; the tumor-initiating properties of miR142-3p SPONGE in pGBM cells were further attenuated by Sox2/AC9 double silencing.

Figure 16:
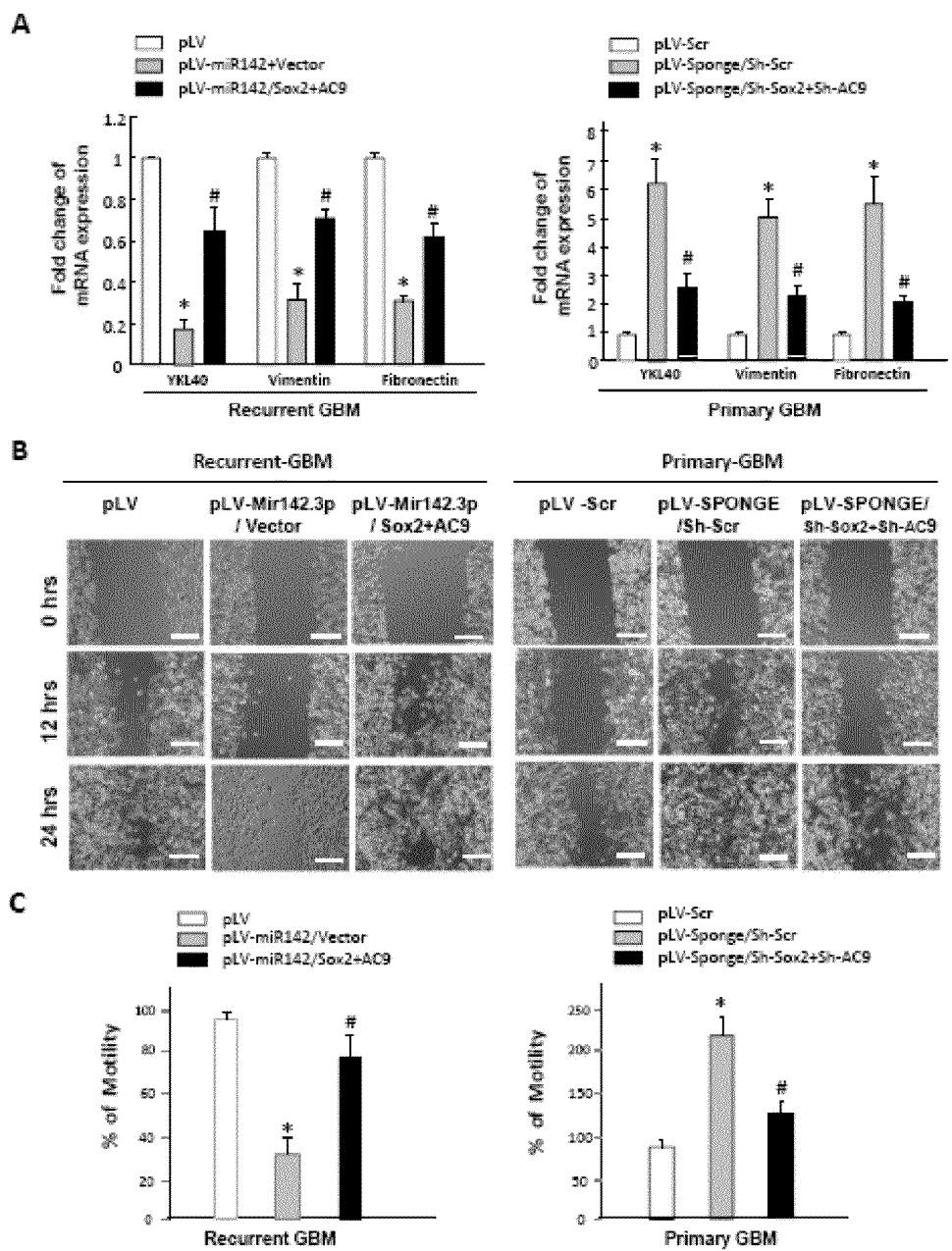

FIGS. 16A-C show that Sox2 and AC9 involved in miR142-3p-mediated mesenchymal transformation: (A) pGBM/Scr, pGBM/Spg, pGBM/Spg/shSox2+shAC9, rGBM/pLV, rGBM/miR142-3p, and rGBM/miR142-3p/Sox2+AC9 cells were subjected to qRT-PCR analyasis of the mesenchymal-favored markers (YKL40, vementin, fibronectin) expression; (B) the wound-healing migration assay was performed with the cells indicated; (C) the activities of motility from the different groups were calculated and presented as a relative value in the chart; *: $p<0.05$, pLV v.s. pLV-miR142/Vector; #: $p<0.05$, pLV-miR142/Vector v.s. pLV-miR142/Sox2+AC9.

DETAILED DESCRIPTION OF THE INVENTION

The present invention will now be described more specifically with reference to the following embodiments, which are provided for the purpose of demonstration rather than limitation.

Glioblastoma (GBM) is the most common primary brain tumor and its prognosis is dismal. Most patients, however, relapse within months after radiochemotherapy. In this invention, expression of miR142-3p was lower in recurrent GBM than in primary GBM, and GBM patients with co-expression of Sox2 and AC9 and suppressed miR142-3p had a worse prognosis and survival. MiR142-3p regulated tumor-initiating properties and mesenchymal transformation in recurrent GBM by targeting Sox2 and AC9. Increased miR142-3p reduced tumorigenicity, mesenchymal transformation and radioresistance in recurrent GBM; while miR142-3p down-regulation promoted tumor-initiating, radioresistant properties and mesenchymal transformation in primary GBM, and appears to be a marker of progression and relapse in GBM patients. Therefore, miR142-3p may be involved in the transcriptional network of CSC reprogramming and mediate mesenchymal transformation in brain tumors. Most importantly, LNA-modified miR142-3p oligos effectively blocked tumor growth and mesenchymal-transitional properties, and synergetically enhanced radiotherapeutic effects in recurrent GBM-derived orthotopic xenografts. To the best of our knowledge, this is the first study to identify miR142-3p as a critical modulator in cancer stem-like property and recurrence in GBM, and suggest that miR142-3p may be a potential clinical prognostic marker as well as a novel miRNA-based approach for GBM treatment.

Figure 4:
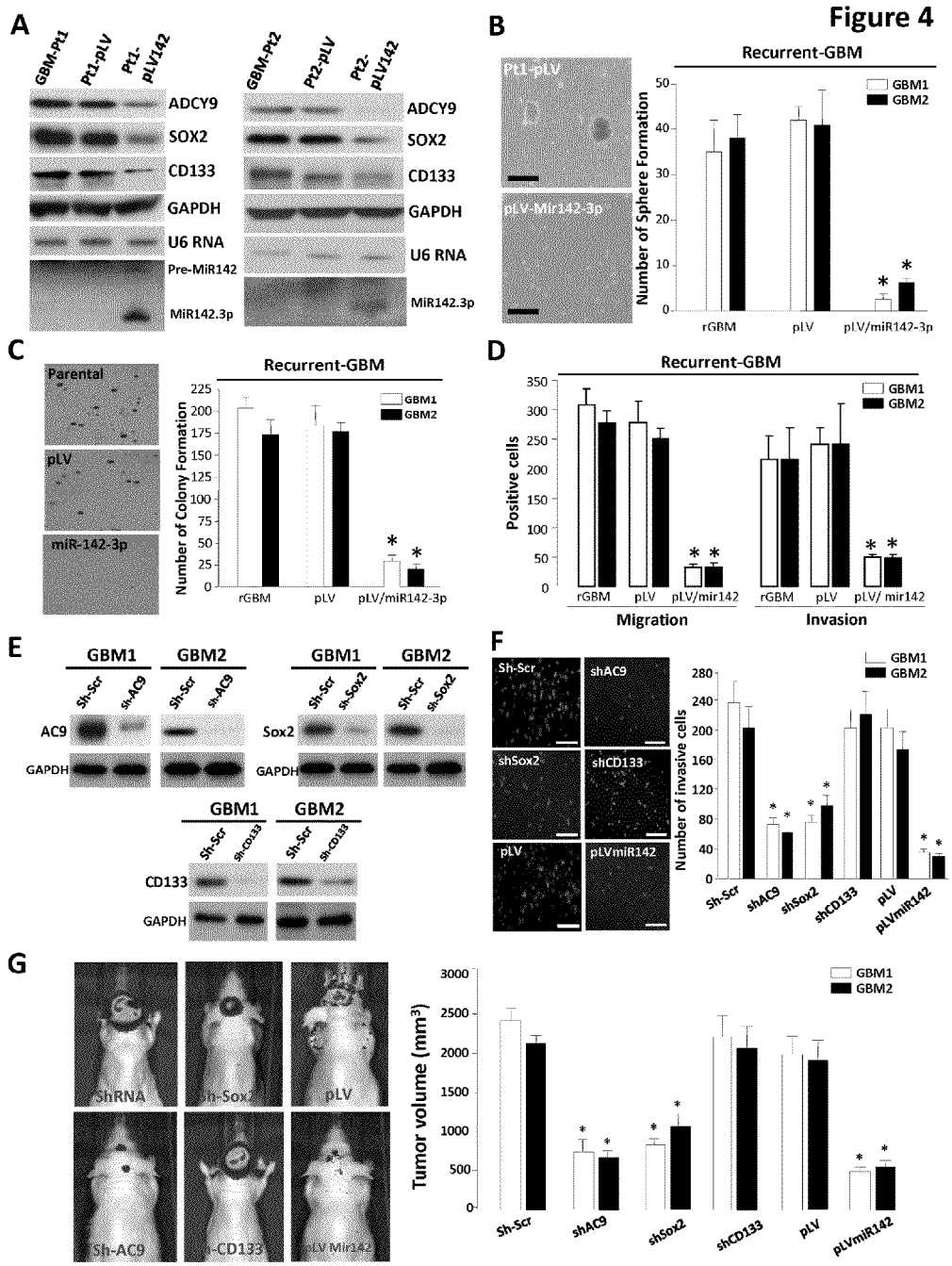
Figure 5:
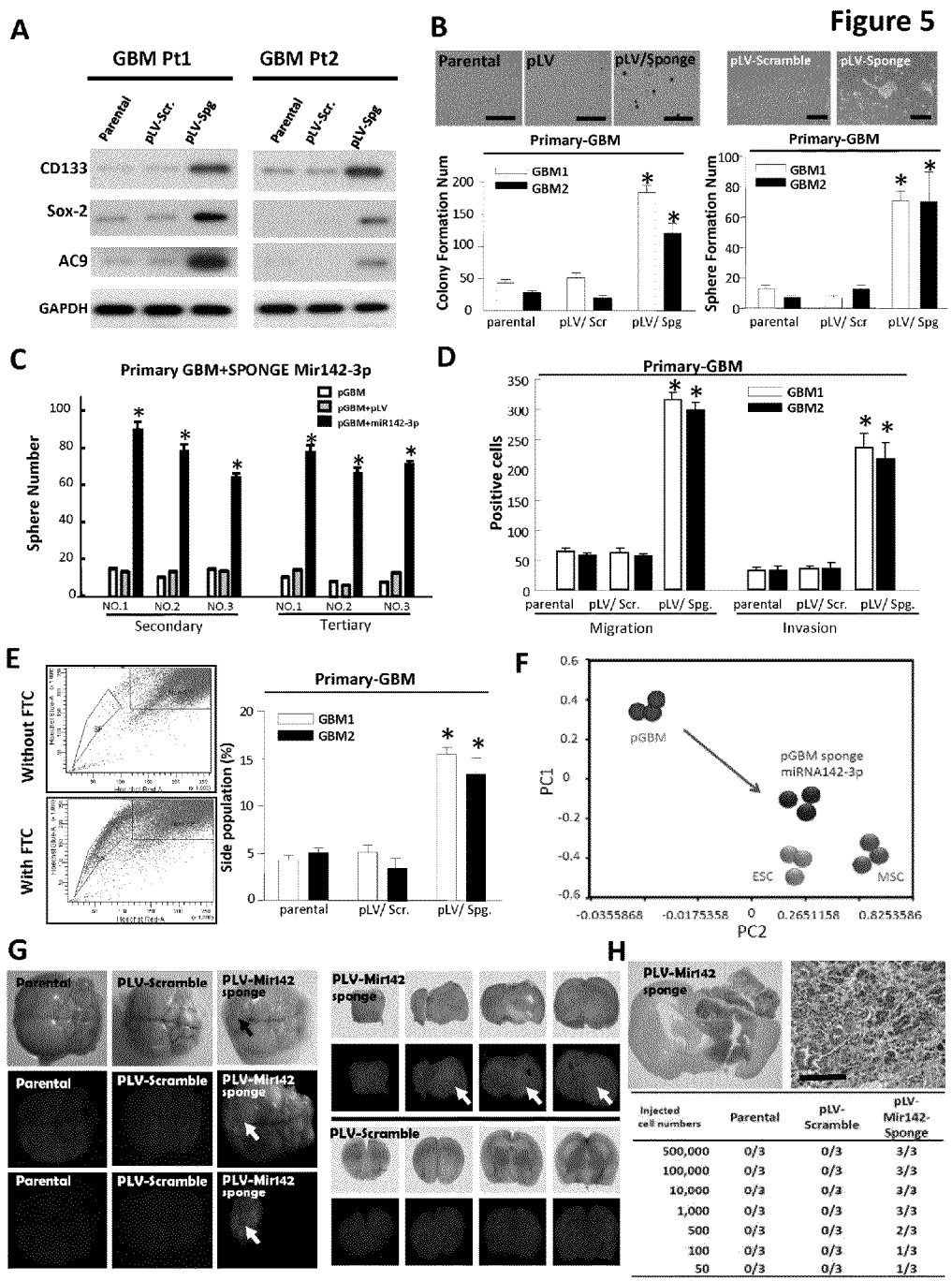
Figure 7:
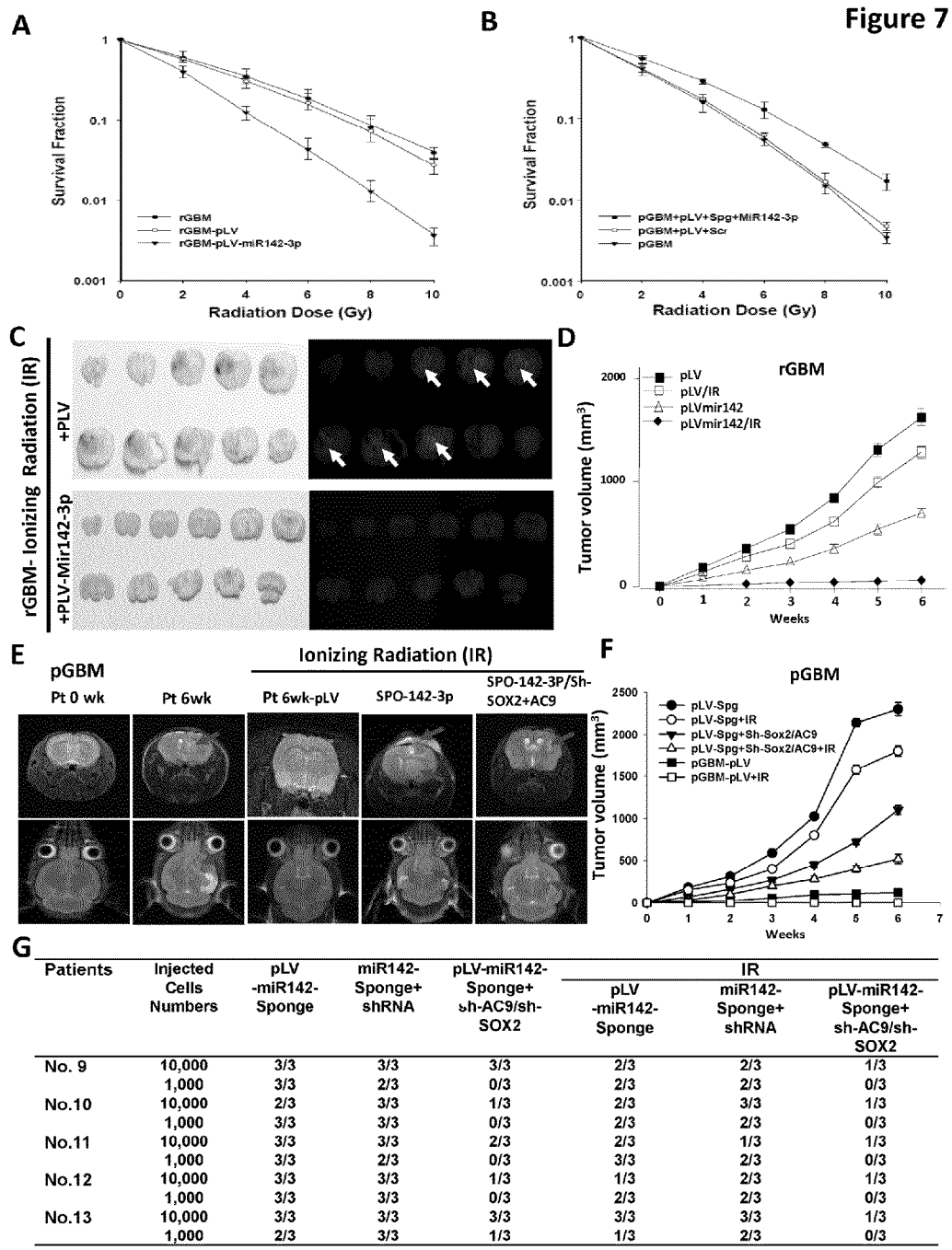

With the increasing awareness of the importance of miR-NAs in tumorigenicity, accumulating evidence has been reported supporting the involvement of miRNAs in CSC-like properties (Garzia et al., 2009; Ji et al., 2009a; Ji et al., 2009b; Silber et al., 2008). For example, ectopic let-7, miR200c, and miR30 expression suppress the tumorigenicity of breast CSCs (Shimono et al., 2009; Yu et al., 2010). Recently, Iliopoulos and colleagues reported that miR200b regulates CSC properties through directly targeting Suz12, a subunit of a polycomb repressor complex (Iliopoulos et al., 2010). In the present study, miR142-3p directly targeted Sox2, AC9, and CD133 3' UTRs and repressed stemness and tumorigenicity by inhibiting Sox2 and AC9 expressions in recurrent GBM cells. Importantly, knockdown of miR142-3p expression significantly activated GBM-CSC self-renewal and repressed pluripotency gene expression. Furthermore, it was showed that SPONGE-miR142-3p increases the in vivo tumor-initiating ability of primary GBM by 10-10000 fold (FIG. 5H and FIG. 15). This evidence supports that downregulation of miR142-3p in GBM leads to stem-like properties that renders GBM cells ability to initiate and regenerate new tumors. Moreover, Sox2 has been shown to play a key role in regulating tumor-initiating properties in glioma stem cells (Gangemi R M, 2009). Overexpression of Sox2 promotes the medulloblastoma tumor-initiating cell and is negatively correlated with medulloblastoma patient survival (Sutter et al., 2010). The data further demonstrates that co-knockdowm of Sox2 and AC9, but not CD133, repressed the tumor-initiating and radioresistant capabilities in GBM cells induced by the down-regulation of miR142-3p (FIGS. 4, 7 and FIG. 15). MiR142-3p appears to negatively regulate stemness gene expression, and reduced miR142-3p expression promotes CSC-related self-renewal and radioresistant properties. Further investigation on miR142-3p-modulated de-differentiation or reprogramming of GBM or GBM-CSC will provide deeper insights on the role of miR142-3p in GBM progression.

Cancer stem cells (CSCs) have been identified in Ewing sarcoma family tumors, which retain mesenchymal stem cell (MSC) plasticity; EWS-FLI-1 and miRNA-145 operate in a mutually repressive feedback loop, identify their common target gene, Sox2, and then initiate MSC reprogramming toward Ewing sarcoma CSCs (Riggi et al.). MiR145 expression is low in self-renewing human embryonic stem cells, and endogenous miR145 represses the 3' UTRs of the pluripotency factors Oot4, Sox2, and Klf4 (Xu et al., 2009). Recently, integrated genomic analysis showed that aberrant gene expressions define the classical, mesenchymal, and pro-neural subtypes of GBM (Verhaak et al.), and further discover a glioma-specific regulatory network involved a transcriptional module that activates mesenchymal gene expression in malignant glioma (Carro et al., 2010). Therefore, miRNAs are likely to regulate self-renewal and mesenchymal properties in brain tumors and GBM-CSCs. The data demonstrated that miR142-3p expression was inversely correlated to GBM progression, and endogenous miR142-3p silencing in pro-neuronal type GBM cells induced them to reprogram into mesenchymal type or CSCs of GBM. Further, Sox2 and AC9 co-expression also regulated mesenchymal properties in GBM. Sox2 and AC9 co-elimination facilitated changing the mesenchymal signature to the pro-neural phenotype in recurrent M-type GBM cells, while Sox2 and AC9 co-overexpression in primary GBM cells reprogrammed the pro-neural phenotype to the mesenchymal signature. Thus, miR142-3p may be the upstream regulator of Sox2 and AC9 in regulating the mesenchymal and pro-neuronal transition. In addition, the molecular signature of high-grade GBM includes glucose as the main neuronal cell energy source and mutation of the IDH1 gene (Zhao et al., 2009). Since cAMP modulates pyruvate dehydrogenase, cAMP may modulate glycolysis pathways and alter the brain's glucose-dependency (Huang et al., 2009). Whether changes in cAMP production and glycolysis metabolic pathways are interconnected with IDH1-mediated TCA cycle blockage is unknown. However, cAMP and IDH1 are involved in glycolysis pathways, and cAMP is a secondary messenger. Thus, finding the AC9 receptors in GBM may help identify novel GBM treatment approaches.

Figure 2:
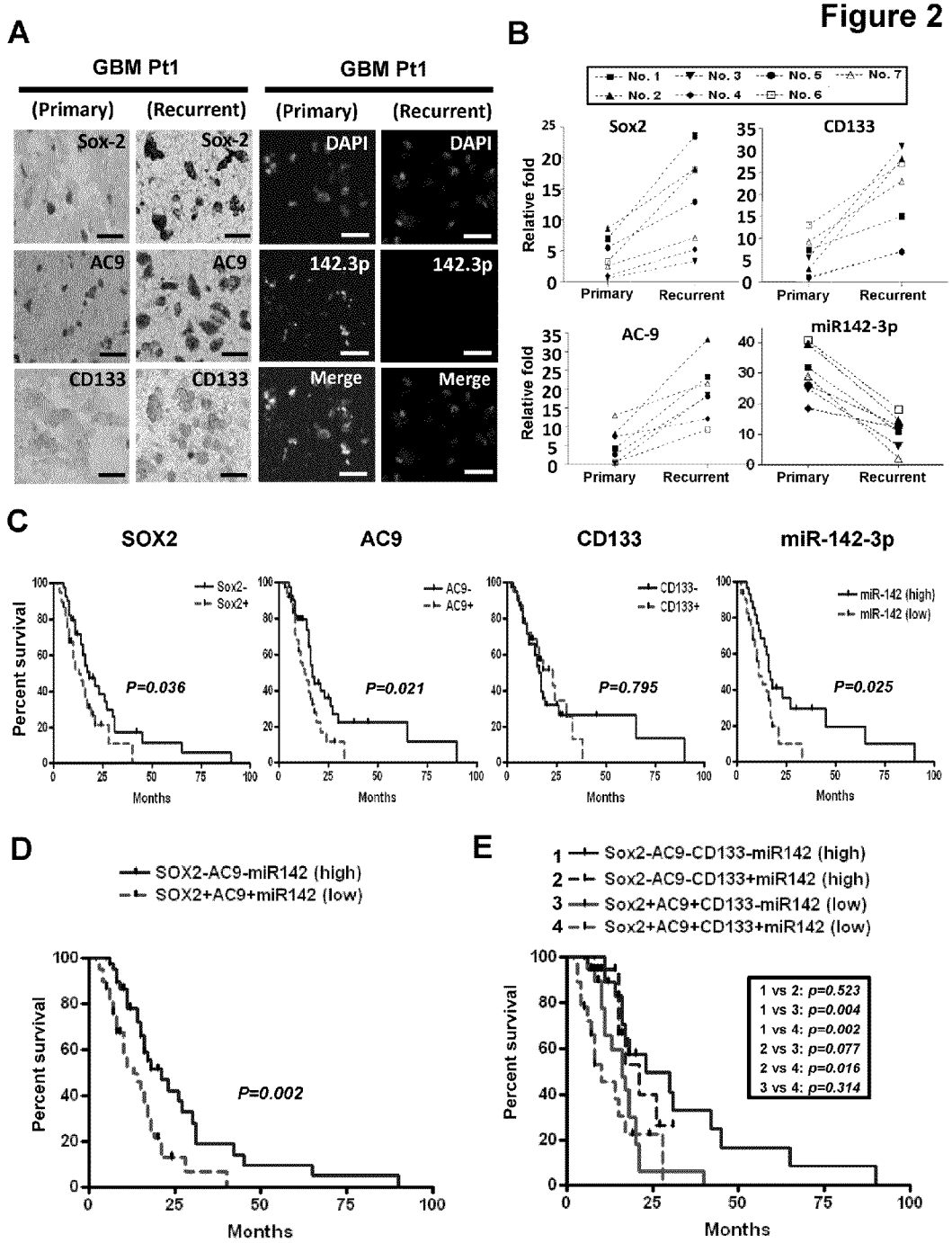

CD133, a 5-transmembrane glycoprotein, is a hematopoietic stem cell and endothelial progenitor marker and appears to be involved in angiogenesis (Corbeil et al., 2000; Hilbe et al., 2004). CD133 expression has been suggested to serve as a prognostic signature for tumor regrowth, malignant progression, and tumor stages in glioma (Zeppernick et al., 2008). A survival finding was recently reported by Pallini et al (Pallini et al., 2010), suggested the percentage of CD133-positive cells in recurrent GBM was increased by 4.6-fold compared with the percentage in primary GBMs, but the increase in CD133 expression was associated significantly with longer survival after tumor recurrence. In this study, the immunohistochemical observation showed that the percentages of CD133-positive cells in recurrent GBM were significantly increased in comparison to primary GBM. But the survival analysis showed that CD133 expression was not associated significantly with survival of GBM (FIG. 2). Notably, CD133 cDNA overexpression in pro-neural type GBM or CD133 silencing with siRNA in mesenchymal type GBM did not affect mesenchymal phenotype expressions or tumorigenic abilities in vitro and in vivo. It's worthwhile to note that CD133$^-$ cells were found to have similar CSC properties in neurosphere initiation efficiencies and clonogenicity compared with CD133$^+$ GBM cells ((Beier et al., 2007); (Joo et al., 2008); (Ogden et al., 2008); (Wang et al., 2008)), and some PTEN-deficient GBM tumors were found to produce both of CD133$^+$ and CD133$^-$ cells of self-renewing tumor-initiating cell types (Chen et al., 2010). Thus, further investigation is needed to determine whether CD133 surface antigen or a CD133-related pathway is involved in regulating stem-like properties, and whether CD133 is a suitable marker for prediction of survival in GBM patients or a therapeutic target in glioma CSCs.

In conclusion, miR142-3p regulates tumor-initiating properties and mesenchymal transformation in GBM. Elevated miR142-3p expression decreases cancer stem-like characteristics and stemness; miR142-3p inhibition enhances the tumorigenic properties of GBM. Thus, miR142-3p may be a novel therapeutic paradigm for brain tumor treatment.

Experimental Procedures

Cell Culture, Isolation of Primary Cell from GBM Tissues and Reagents

All procedures of tissues acquirements are following the tents of the Declaration of Helsinki and are reviewed by Institutional Review Committee at Taipei Veterans General Hospital. In brief, after surgical removal of the GBM tissues, the tissues were washed 3 times in glucose containing HBSS and then the sample were sliced at thickness of 300 mm and the sliced tissues were immersed in 0.1% (w/w) collagenase containing glucose containing HBSS for 15 minutes at 37° C. and rotation shaker shaking at 125 rpm. GBM primary culture and GBM cell lines were cultured in MEM (Invitrogen, Carlsbad, Calif., USA) with 10% fetal bovine serum, supplemented with 1 mM sodium pyruvate, non-essential amino acids, 2 mM L-glutamine, 100 units/mL penicillin, and 100 µg/mL streptomycin under standard culture conditions (37° C., 95% humidified air, 5% $CO_2$).

Enrichment of Cancer Stem-Like Cells and Isolation of CD133-Positive Cells

All procedures of tissues acquirements are following the tents of the Declaration of Helsinki and are reviewed by Institutional Review Committee at Taipei Veterans General Hospital. In brief, after surgical removal of the head and neck cancer tissues, the tissues were washed 3 times in glucose containing HBSS and then the sample were sliced at thickness of 300 mm and the sliced tissues were immersed in 0.1% (w/w) collagenase containing glucose containing HBSS for 15 minutes at 37° C. and rotation shaker shaking at 125 rpm. Then collagenase digested cells were centrifuged at 100×g for 10 minutes and the cells were re-suspended in cancer stem cell enriching medium: DMEM/F12 medium supplementary with serum-free DMEM/F12 (GIBCO) medium supplemented with N2 supplement (R&D), 10 ng/mL human recombinant bFGF (R&D) and 10 ng/ml EGF for culturing GBM cells.

For isolating CD133-positive cell, the procedure was as followed. Dissociated cells from tumor samples of GBM patients were labeled with 1 mL CD133/1 micromagnetic beads/$10^6$ cells using a CD133 cell isolation kit (MACS, Miltenyi Biotec). CD133$^+$ cells were cultured in serum-free DMEM/F12 (GIBCO) medium supplemented with N2 supplement (R&D,), 10 ng/mL human recombinant bFGF (R&D), and 10 ng/ml EGF (Chiou et al., 2008; Kao et al., 2009; Kota et al., 2009).

Radiation Treatment for Cell Survival Analysis

Gamma radiation (ionizing radiation; IR) was delivered by Theratronic cobalt unit T-1000 (Theratronic International, Inc., Ottawa, Canada) at a dose rate of 1.1 Gy/min (SSD=57.5 cm). Cells in the control and IR groups were exposed to different dosages (0, 2, 4, 6, 8, and 10 Gy). After a 10-day incubation, colonies (>50 cells per colony) were fixed and stained for 20 minutes with a crystal violet and methanol solution. Cell survival was determined with a colony formation assay. Plating efficiency (PE) and survival fraction were calculated as: PE=(colony number/inoculating cell number)×100%; SF=colonies counted/(cells seeded×(PE/100)).

Tumorsphere-Forming Assay

Tumor cells were dissociated and cultured as tumorspheres in modified DMEM/F-12 supplemented with N2 (R&D), 10 ng/mL epidermal growth factor (EGF, Invitrogen), 10 ng/mL basic fibroblast growth factor (bFGF, Invitrogen), and penicillin/streptomycin at $2 \times 10^6$ live cells/75 $cm^2$ flask. Tumorsphere numbers were scored after 14 days.

Quantitative RT-PCR

Total RNA was prepared from cells or tissues using Trizol reagent according to the manufacturer's protocol (Invitrogen). qRT-PCRs of mRNAs were reverse-transcribed using the Superscript III first-strand synthesis system for RT-PCR (Invitrogen). qRT-PCR reactions on resulting cDNAs were performed on an ABI 7900HT (Applied Biosystems). Primer sequences are listed in Table 1 (SEQ ID NOS. 1-24).

TABLE 1

The sequences of the primers for quantitative RT-PCR

| Gene (Accession No.) | Primer Sequence (5' to 3') | Product size (bp) | Tm (° C.) |
|---|---|---|---|
| ADCY9 (NM_001116) | F: GCTTCTTTCTGTTTACCTTCACCAA (SEQ ID NO. 1)<br>R: ATAGAGCAAAAAGAGCACTTCGATG (SEQ ID NO. 2) | 223 | 55 |

TABLE 1 -continued

The sequences of the primers for quantitative RT-PCR

| Gene (Accession No.) | Primer Sequence (5' to 3') | Product size (bp) | Tm (° C.) |
|---|---|---|---|
| CD133 (NM_006017) | F: CGTGATTTTTTACTACCTGGGCTTA (SEQ ID NO. 3)<br>R: AGCCTCGGGTGGTCGG (SEQ ID NO. 4) | 77 | 55 |
| CHI3L1(YKL40) (NM_001276) | F: CTCTGCATACAAACTGGTCTGCTAC (SEQ ID NO. 5)<br>R: TAGATGATGTGGGTACAGAGGAAGC (SEQ ID NO. 6) | 111 | 55 |
| Fibronectin (NM_212482) | F: ACCTGAGTCCCGGCCTGGAGTA (SEQ ID NO. 7)<br>R: CTCAGGCCGATGCTTGAATCGGT (SEQ ID NO. 8) | 151 | 55 |
| GFAP (NM_002055) | F: ATCGCCACCTACAGGAAGCT (SEQ ID NO. 9)<br>R: GCATCTCCACGGTCTTCACC (SEQ ID NO. 10) | 160 | 55 |
| KLF-4 (NM_004235) | F: CCGCTCCATTACCAAGAGCT (SEQ ID NO. 11)<br>R: ATCGTCTTCCCCTCTTTGGC (SEQ ID NO. 12) | 76 | 60 |
| MAP2 (NM_002374) | F: GTCAGGGTCCCACAGCGTGC (SEQ ID NO. 13)<br>R: GCCTGGGCTTCAGCTGCCTC (SEQ ID NO. 14) | 114 | 55 |
| Nanog (NM_024865) | F: ATTCAGGACAGCCCTGATTCTTC (SEQ ID NO. 15)<br>R: TTTTTGCGACACTCTTCTCTGC (SEQ ID NO. 16) | 76 | 60 |
| Nestin (NM_006617) | F: AGGAGGAGTTGGGTTCTG (SEQ ID NO. 17)<br>R: GGAGTGGAGTCTGGAAGG (SEQ ID NO. 18) | 112 | 55 |
| Oct-4 (NM_002701) | F: GTGGAGAGCAACTCCGATG (SEQ ID NO. 19)<br>R: TGCTCCAGCTTCTCCTTCTC (SEQ ID NO. 20) | 86 | 60 |
| Sox2 (NM_003106) | F: CGAGTGGAAACTTTTGTCGGA (SEQ ID NO. 21)<br>R: TGTGCAGCGCTCGCAG (SEQ ID NO. 22) | 74 | 55 |
| Vimentin (NM_003380) | F: GCAATCTTTCAGACAGGATGTTGAC (SEQ ID NO. 23)<br>R: GATTTCCTCTTCGTGGAGTTTCTTC (SEQ ID NO. 24) | 118 | 55 |

For miRNAs, qRT-PCR was performed using TaqMan miRNA assays with specific primer sets. All reagents and protocols were from Applied Biosystems, and detection was performed using a 7900HT fast real-time PCR system. Used primers are listed in Table 2 (SEQ ID NOS. 1-24).

Plasmid Constructions

All plasmids had been validated and sequenced. The SOX2, ADCY9, and CD133 3' UTRs were amplified by PCR and were cloned into the pMIR-REPORT vector (Applied Biosystems). Serial deletion constructs were generated by primer sets for Sox2 (SEQ ID NOS. 25-29), ADCY9 (SEQ ID NOS. 30-35), and CD133 3' UTRs (SEQ ID NOS. 36-41) (Table 3).

Various SOX2, ADCY9, and CD133 3' UTR regions were amplified by PCR by proofreading-Taq. MluI/HindIII or SpeI/PmeI restriction cutting sites were introduced by primers with additional restriction enzyme cutting sites; amplified regions were digested with MluI/HindIII or SpeI/PmeI and then subcloned into pMIR-luciferase reporter plasmids. Oligos for miR142-3p sponge, miR142-3p antisense and scramble construction are listed in Table 3 (SEQ ID NOS.42-52). Oligos were annealed and ligated into BLOCK-iT Pol II miR RNAi expression vectors as described by (Gangemi et al., 2009). Oligonucleotides targeting human SOX2 sequence were designed on the Invitrogen website. One oligonucleotide was chosen for cloning into BLOCK-iT Pol II miR RNAi expression vectors as described by (Gangemi et al., 2009). Construction primers (SEQ ID NOS. 42-52) are listed in Table 3. The pcDNA 6.2-GW/EmGFP-miR-neg control plasmid contains an insert that can form a hairpin structure that is processed into mature miRNA, but is predicted not to target any known vertebrate gene. The negative control sequence without 5' overhangs is shown in Table 3. All cloning procedures were performed following the manufacturer's instructions.

Flow Cytometry

Cells were stained with anti-CD133 antibody conjugated to phycoerythrin (Miltenyi Biotech., Auburn, Calif., USA), with labeling according to the manufacturer's instructions. Red (>650 nm) fluorescence emission from 10,000 cells illuminated with blue (488 nm) excitation light was measured with a FACSCalibur (Becton Dickinson) using CellQuest software. In cell-sorting experiments, cells were labeled and sorted using FACSAria (BD Biosciences).

MiR142-3p Angomir and Lipsome Mediated Delivery

MiR142-3p RNA oligoes were synthesized as identical sequences of miR142-3p with modifications. The phosphodiester backbones were modified by phosphothiolate backbones and the ribose was replaced by lock-nucleic-acid (LNA) ribose. The delivery of the miR142-3p angomir was mediated by liposome-based nucleic acid delivery method. In brief, miR142-3p was dissolved in D5W (5% dextrose water) and packaged with specialized lipid components into liposomes. The packaged liposomes (final concentraction of miR142-3p angomir is 10 ng/μL) were delivered into the same locus of intracranially xenotransplanted tumor-initiation cells.

miRNA Northern Blotting

MicroRNAs were extracted by the miVana miRNA isolation kit (Ambion) or Trizol (Invitrogen). 50 ng of isolated small RNAs were electrophoresed in each well in 7M urea containing 15% polyacrylamide gel in 0.5×TBE. After electrophoresis, small RNAs were transferred to Hybond-N+ membrane by semi-dry transfer and cross-linked by UV crosslinker. RNA decade markers were synthesized using the miVana probe and marker kit, and LNA-RNA oligos (SEQ ID NO.52) (Table 3) specific to miR142-3p were labeled by the same kit for introducing 5' end radioisotope labeling. Membranes were prehybridized and hybridized in hybridization buffer for 24 h and washed three times with wash buffer. Hybridization signals were exposed to X-ray film for 48 h.

Fluorescence In Situ Hybridization (FISH)

Cells were fixed in 4% paraformaldehyde with PBS at room temperature for 15 min, and then permeabilized with 0.1% NP-40 and 0.1% X-100 Triton in PBS. After blocking with 10% donkey serum for 2 h at room temperature, LNA-modified, FITC-conjugated miR142-3p antisense oligos (SEQ ID N0.52) were applied to the hybridization buffer at 42° C. overnight, then washed with 5×SSPE and 2×SSPE. Staining images were acquired by Olympus imaging systems (Silahtaroglu et al., 2007). Oligo sequences (SEQ ID NO. 52) are listed in Table 2.

TABLE 2

Primers for wild type sequence and deletion mutants of 3'UTR

| SOX2 3'UTR | SOX2-WT-F | 5'-ATGCACGCGTGGGCCGGACAGCGAACTGGAGGGGG-3' (SEQ ID NO. 25) |
| | SOX2-D1 | 5'ATGCAAGCTTACAATAAATTTACAGAAATATTACA3' (SEQ ID NO. 26) |
| | SOX2-D4 | 5'ATGCAAGCTTATACAAGGTCCATTCCCCCGCCCTC3' (SEQ ID NO. 27) |
| | SOX2-D5 | 5'ATGCAAGCTTTTCTTTTTGAGCGTACCGGGTTTTC3' (SEQ ID NO. 28) |
| | SOX2-WT-R | 5'-GGAAGCTTTTTCAGTGTCCATATTTCAAAAATT-3' (SEQ ID NO. 29) |
| ADCY9 3'UTR | ADCY9-WT-F | 5'-ATGCACTAGTGGCGGCGCCCACCCGCTGCCCGAGG-3' (SEQ ID NO. 30) |
| | ADCY9-D1 | 5'-ATGCGTTTAAACTGGCTGTTTAGGAAGGCTCAGGG-3' (SEQ ID NO. 31) |
| | ADCY9-D2 | 5'-ATGCGTTTAAACCAACTCCGACCGGACAACTCGGG-3' (SEQ ID NO. 32) |
| | ADCY9-D3 | 5'-ATGCGTTTAAACACACAAAAGAGACATCTGGTTAC-3' (SEQ ID NO. 33) |
| | ADCY9-D4 | 5'-ATGCGTTTAAACTGCGCATGTGTGCTTACATAGAG-3' (SEQ ID NO. 34) |
| | ADCY9-WT-R | 5'-ATGCGTTTAAACTTTTTTTTATTTAAATTTTAGAATA-3' (SEQ ID NO. 35) |
| CD133 3'UTR | CD133-WT-F | 5'-AGTCACGCGTAGCATCAGGATACTCAAAGTGGAAA-3' (SEQ ID NO. 36) |
| | CD133-D1 | 5'-ATGCAAGCTTCATGCAAATTTAGGGACCAAACTCA-3' (SEQ ID NO. 37) |
| | CD133-D2 | 5'-ATGCAAGCTTTAAAACAACTCCACTTTTGAACGAA-3' (SEQ ID NO. 38) |
| | CD133-D4 | 5'-ATGCAAGCTTTAGAATCTAGCCATCACATTTGATA-3' (SEQ ID NO. 39) |
| | CD133-D5 | 5'-ATGCAAGCTTCCAGAGACCAATGGTGCCGTTGCCT-3' (SEQ ID NO. 40) |
| | CD133-WT-R | 5'-GGAAGCTTCCAAGTTCCTTTTTATTCAAATGAA-3' (SEQ ID NO. 41) |

Primers for Sponge and Antisense of miR142-3p and Scramble constructions

| SPONGE FORWARD | 5'-GATCCTCCATAAAGTACTTACACTACAAGATCTGGCCGCAC-3' (SEQ ID NO. 42) |
| SPONGE REVERSE | 5'-TCGAGTGCGGCCAGATCTTGTAGTGTAAGTACTTTATGGAG-3' (SEQ ID NO. 43) |
| ANTISENSE FORWARD | 5'TGCTGTCCATAAAGTAGGAAACACTACAGTTTTGGCCACTGACTGAC-TGTAGTGTCCTACTTTATGGA-3' (SEQ ID NO. 44) |
| ANTISENSE REVERSE | 5'-CCTGTCCATAAAGTAGGACACTACAGTCAGTCAGTGGCCAAAACTG-TAGTGTTTCCTACTTTATGGAC-3' (SEQ ID NO. 45) |
| SCRAMBLE FORWARD | 5'-GATCCCATTAATGTCGGACAACTCAATCAGATCTGGCCGCAC-3' (SEQ ID NO. 46) |
| SCRAMBLE REVERSE | 5'-TCGAGTGCGGCCAGATCTGATTGAGTTGTCCGACACATTAATGG-3' (SEQ ID NO. 47) |

Northern blotting for detection miR142-3p expression Locked nuclear Acid modified Anti-sense miR142-3p (SEQ ID NO. 52)
miR142-3p antisense 5'-UCCAUAAAGUAGGAAACACUACA-3'

In Situ Hybridization for detection miR142-3p expression Locked nuclear Acid modified Anti-sense miR142-3p conjugated FITC (SEQ ID NO. 52)
miR142-3p antisense 5'-UCCAUAAAGUAGGAAACACUACA-3'

Target Sequence of lentiviral-based Sh-RNA

Target Sequence for ADCY9-knockdown (Sh-RNA)

Target Sequence 5'-GCCCAGACAGTTCTGTATTAA-3' (SEQ ID NO. 48)

Target Sequence for CD133-knockdown (Sh-RNA)
Target Sequence 5'-GCGTCTTCCTATTCAGGATAT-3' (SEQ ID NO. 49)

-continued

```
Primers for sox2-knockdown (Sh-RNA) plasmid construction

FORWARD PRIMER   5'-TGCTGTGGTCATGGAGTTGTACTGCAGTTTTGGCCACTGACTGACTG-
                 CAGTACCTCCATGACCA-3' (SEQ ID NO. 50)

REVERSE PRIEMR   5'-CCTGTCCATAAAGTAGGACACTACAGTCAGTCAGTGGCCAAAACTGT-
                 AGTGTTTCCTACTTTATGGAC-3' (SEQ ID NO. 51)
```

Immunoblotting Assay

Cell protein extraction and immunoblotting analysis were performed as described (Kao et al., 2009). 15 µL of sample was boiled at 95° C. for 5 min and separated on 10% SDS-PAGE. The proteins were transferred to Hybond-ECL nitrocellulose paper or PVDF membrane (Amersham, Arlington Heights, Ill., USA) by wet-transfer. Primary and secondary antibodies were added as indicated. Reactive protein bands were detected by the ECL detection system (Amersham). Used antibodies are listed in Table 3.

TABLE 3

List of proteins tested by antibodies

| Protein | Assay | Antibody | Origin | Dilution | Incubation period |
|---|---|---|---|---|---|
| ADCY9 | WB, IHC | rpab | ab14783, Abcam, Inc | 1:1000 | overnight |
| actin | WB | mmab | mAB1501, Millipore, Inc | 1:10000 | 60 min |
| CD133 | WB, IHC | rpab | #3663, Cell Signaling Technology, Inc. | 1:1000 | overnight |
| YKL40(CHL3L1) | WB | rpab | Ab88847, Abcam, Inc | 1:1000 | 60 min |
| COL5A1 | WB | rpab | sc-20648, Santa Cruz, Inc | 1:200 | 60 min |
| Fibronectin | WB | rpab | AB1954, Millipore, Inc | 1:1000 | overnight |
| GAPDH | WB | rpab | Ab9385, Abcam, Inc | 1:5000 | 60 min |
| Nestin | WB | rpab | AB5922, Millipore, Inc | 1:1000 | 60 min |
| SOX2 | WB, IHC | rpab | #2748, Cell Signaling Technology, Inc. | 1:1000 | overnight |
| Vimentin | WB | mmab | #3390, Cell Signaling Technology, Inc. | 1:2000 | overnight |

Abbreviations: WB, Western blot; mmab, mouse monoclonal antibody; rpab, rabbit polyclonal antibody Immunofluorescence Staining Cells were subcultured on cover slides, fixed with 4% paraformaldehyde, permeabilized with 0.1% Triton X-100, and immuno-stained with the indicated antibodies, followed by FITC- or PE-labeled secondary antibodies for imaging.

Immunohistochemistry for GBM Tissues

Patients' tissue samples were spotted on glass slides for immunohistochemical staining. After deparaffinization and rehydration, tissue sections were processed with antigen retrieval by 1% Trilogy diluted in $H_2O$ (Biogenics) with heating. The slides were immersed in 3% $H_2O_2$ for 10 minutes and washed with PBS three times. Tissue sections were blocked with serum (Vestastain Elite ABC kit, Vector Laboratories, Burlingame, Calif., USA) for 30 minutes, then incubated with the primary antibody anti-human CD133 and mouse anti-human Sox2 (Cell Signaling Technology) in PBS solution at room temperature for 2 hours. Tissue slides were washed with PBS and incubated with biotin-labeled secondary antibody for 30 min, then incubated with streptavidin-horse radish peroxidase conjugates for 30 min, and washed with PBS three times. Tissue sections were then immersed with chromogen 3-3'-diaminobenzidine plus $H_2O_2$ substrate solution (Vector® DBA/Ni substrate kit, SK-4100, Vector Laboratories) for 10 minutes. Hematoxylin was applied for counter-staining (Sigma Chemical Co.,) Finally, the tumor sections were mounted with a cover slide with Gurr® (BDH Laboratory Supplies, UK) and examined under a microscope. Pathologists scoring the immunohistochemistry were blinded to the clinical data. The interpretation was done in five high-power views for each slide, and 100 cells per view were counted for analysis.

In Vitro Soft Agar Assay

A 24-well plate Transwell® system with a polycarbonate filter membrane (8-µm pore size; Corning, United Kingdom) was used. Cell suspensions were seeded in the chamber's upper compartment, with $1 \times 10^5$ cells in 100 µL serum-free medium. The opposite surface of the filter membrane, facing the lower chamber, was stained with Hoechst 33342 for 3 min, and migrating cells were visualized under an inverted microscope. For the soft agar assay, the bottom of each well (35 mm) of a 6-well culture dish was coated with a 2-mL agar mixture (DMEM, 10% (v/v) FCS, 0.6% (w/v) agar). After the bottom layer solidified, a 2-mL top agar-medium mixture (DMEM, 10% (v/v) FCS, 0.3% (w/v) agar) containing $2 \times 10^4$ cells was added and incubated at 37° C. for 4 weeks. The plates were stained with 0.5 mL 0.005% Crystal Violet, and the number of colonies was counted using a dissecting microscope.

In Vitro Cell Invasion Analysis.

The 24-well plate Transwell® system with a polycarbonate filter membrane of 8-µm pore size (Corning, United Kingdom) was employed to evaluate the invasion ability of cells. The membrane was coated with Matrigel™ (BD Pharmingen, N.J., USA). The cancer cell suspensions were seeded to the upper compartment of the Transwell chamber at the cell density of $1 \times 10^5$ in 100 µl within serum-free medium. The lower chamber was filled with serum-free medium. or media with 10% serum After 24 hours of incubation, the medium was removed and the filter membrane was fixed with 4% formalin for 1 hour. Subsequently, the remaining cells of the filter membrane faced the lower chamber was stained with Hoechst 33258 (Sigma-Aldrich). The migrated cancer cells were then visualized and counted from 5 different visual areas of 100-fold magnification under an inverted microscope.

In Vivo Analysis of Tumor Growth and Metastasis

All animal procedures were in accordance with the institutional animal welfare guidelines of Taipei Veterans General Hospital. 2×10$^5$ GBM cells were injected into the striatum of the brains of 8-week-old SCID mice (BALB/c strain). In vivo GFP imaging was performed using an illuminating device (LT-9500 Illumatool TLS, equipped with excitation illuminating source [470 nm] and filter plate [515 nm]) (Kao et al., 2009). Tumor size was measured using calipers. Tumor volume was calculated using the formula, (length×width$^2$)/2, and analyzed using Image Pro-plus software (Kao et al., 2009).

Bioluminescence Imaging (BLI) and 3T-MRI

All procedures involving animals were in accordance with the institutional animal welfare guidelines of the Taipei Veterans General Hospital. Eight-week-old nude mice (BALB/c strain) were injected with different number of cells orthotopically. BLI was performed using an IVIS50 animal imaging system (Xenogen Corp.). The photons emitted from the target site penetrated through the mammalian tissue and could be externally detected and quantified using a sensitive light-imaging system. The image acquisition time was 1 min. The displayed images of the tumor sites were drawn around and quantified in photons per second using Living Image software (Xenogen Corp.). Tumor size was measured in each mouse at weekly intervals using a 3T MR imaging Biospect system (Bruker) with a mini quadrature coil (12-cm inner diameter) for radiofrequency transmission and reception of MR imaging signals (Chiou et al., 2006). The volume was calculated (according to the following formula: [length×width$^2$]/2), and then analyzed using Image-Pro Plus software.

Microarray Analysis and Bioinformatics

Total RNA was extracted from cells using Trizol reagent (Life Technologies, Bethesda, Md., USA) and the Qiagen RNeasy (Qiagen, Valencia, Calif., USA) column for purification. Total RNA was reverse-transcribed with Superscript II RNase H-reverse transcriptase (Gibco BRL) to generate Cy3- and Cy5-labeled (Amersham Biosciences Co., Piscataway, N.J., USA) cDNA probes for the control and treated samples, respectively. The labeled probes were hybridized to a cDNA microarray containing 10,000 gene clone immobilized cDNA fragments. Fluorescence intensities of Cy3 and Cy5 targets were measured and scanned separately using a GenePix 4000B Array Scanner (Axon Instruments, Burlingame, Calif., USA). Data analysis was performed using GenePix Pro 3.0.5.56 (Axon Instruments, USA) and GeneSpring GX 7.3.1 software (Agilent, Palo Alto, Calif.). The average-linkage distance was used to assess the similarity between two groups of gene expression profiles as described below. The difference in distance between two groups of sample expression profiles to a third was assessed by comparing the corresponding average linkage distances (the mean of all pair-wise distances (linkages) between members of the two groups concerned). The error of such a comparison was estimated by combining the standard errors (the standard deviation of pair-wise linkages divided by the square root of the number of linkages) of the average linkage distances involved. Classical multidimensional scaling (MDS) was performed using the standard function of the R program to provide a visual impression of how the various sample groups are related.

Statistical Analysis

Data are presented as mean±SD. A Student's t test or analysis of variance (ANOVA) test was used to compare the continuous variables between groups, as appropriate. The chi-square test or Fisher's exact test was used to compare the categorical variables. Survivals were estimated by the Kaplan-Meier method and compared by the log-rank test. $P<0.05$ was considered statistically significant.

EXAMPLES

Example 1

Clinical Significance of miR142-3p Expression in Recurrent GBM

Figure 1:
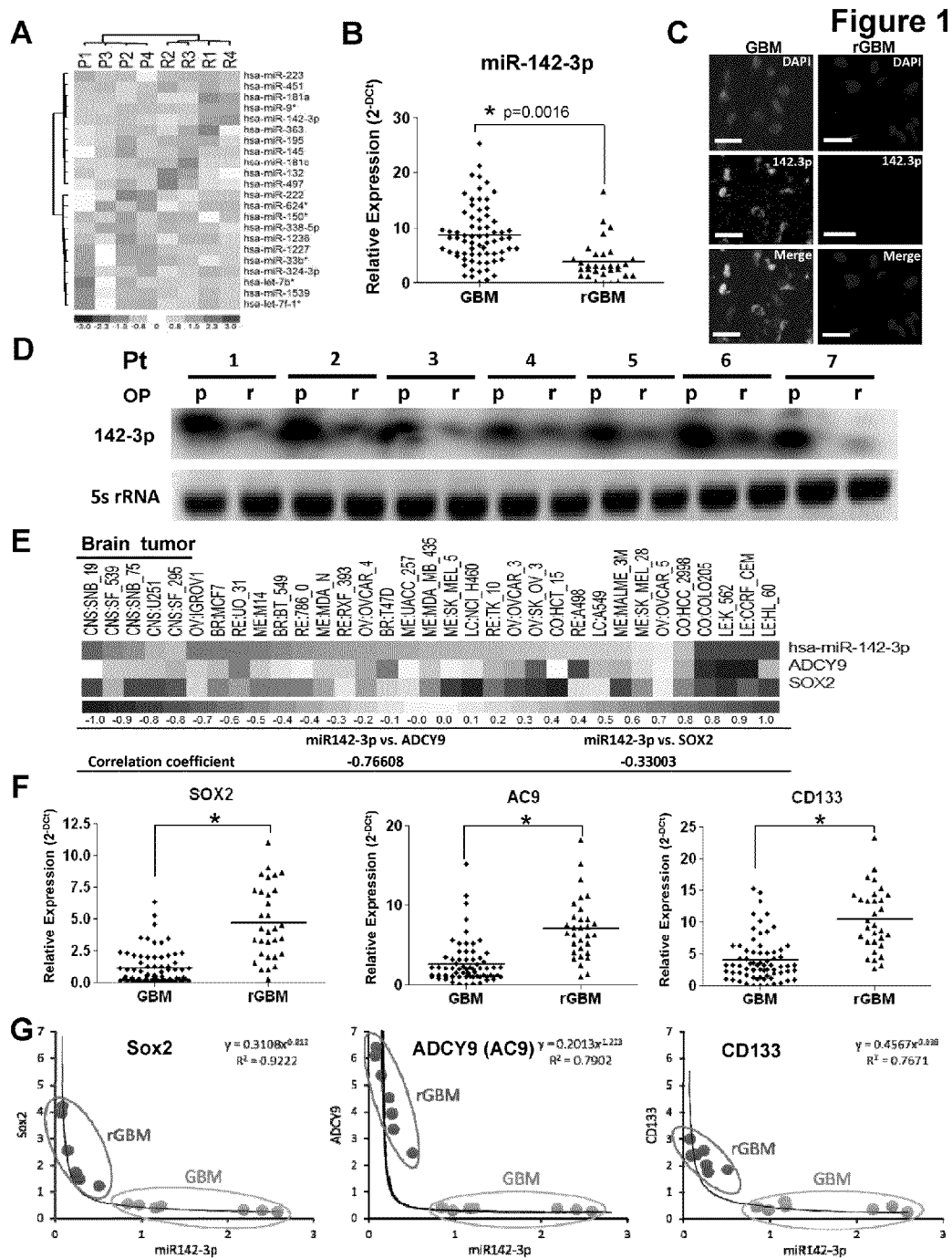

Glioblastoma multiforme (GBM) bears a very dismal prognosis with a rapid evolution and relapse within the first year even with complete resection followed by adjuvant chemoradiation. Some studies have suggested that these aggressive and recurrent GBM may be attributed to the persistence of cancer stem cells (CSC) (also known as tumor initiating cells (TIC)). A recent study has shown that microRNAs are involved in regulating or activating CSC properties in malignant cancers. However, the role that microRNAs play in modulating or generating CSCs in GMB, leading to relapse and resistance to conventional therapeutics, is still blurred. This invention sought to answer this critical question by elucidating the role of miRNAs in GBM recurrence. Initially, the miRNA expression profiles between primary and recurrent GBM from the same patient in four independent cases were compared, and it was found that 22 miRNAs were diversely expressed (up or down) between primary and recurrent specimens (total of four patient pairs; FIG. 1A). To further validate the microarray data, 70 primary and 30 recurrent GBM patient specimens (Table 4) were collected and the expression levels of these 22 miRNAs by quantitative RT-PCR were analyzed (FIG. 9). MiR142-3p demonstrated the most significant difference between primary and recurrent GBMs (FIG. 1B; FIG. 9A).

TABLE 4

Clinical Characteristics of GBM patients

|  | GBM | Recurrent GBM |
|---|---|---|
| No. of patients | 70 | 30 |
| Age (years) |  |  |
| Median | 52 | 54 |
| Sex |  |  |
| Female | 31 | 12 |
| Male | 39 | 18 |
| Age at diagnosis |  |  |
| Median | 48 | 51 |
| Survival (months) |  |  |
| Median (CI) | 13.6 | 2.8 |
| KPS |  |  |
| 100 | 0 | 0 |
| 80-100 | 29 | 6 |
| <80 | 41 | 24 |
| P53 mutation |  |  |
| Yes | 28 | 27 |
| No | 42 | 3 |
| MGMT methylated |  |  |
| Yes | 30 | 18 |
| No | 40 | 12 |

TABLE 4-continued

Clinical Characteristics of GBM patients

|  | GBM | Recurrent GBM |
|---|---|---|
| Surgery |  |  |
| Total gross removal | 27 | 8 |
| Subtotal removal | 42 | 21 |
| No surgery | 1 | 1 |
| Radiation |  |  |
| Yes | 70 | 30 |
| No | 0 | 0 |
| Treatment with Temodal ® |  |  |
| Yes | 70 | 30 |
| No | 0 | 0 |

Fluorescent in situ hybridization (FISH) detected a high expression level of miR142-3p in primary GBM, whereas miR142-3p was undetectable by FISH in recurrent GBM tumor tissue (FIG. 1C). Moreover, miR142-3p expression was analyzed in 7 pairs (the previously described 4 pairs plus 3 additional pairs) of primary and recurrent GBM tissues (tumor samples excised from the first and second operations of 7 GBM patients) by northern blotting. MiR142-3p expression was lower in tumor samples excised from the second operations, than the first ones (FIG. 1D), suggesting low miR142-3p expression was inversely correlated with tumor relapse and progression.

The discovery of the association between low expression of miR142-3p and GBM relapse suggests the possibility that miR142-3p may regulate the stemness or CSC-like properties of GBM cells, possibly through downstream targets that are related to a stem cell mechanism or signature. To investigate the potential downstream targets of miR142-3p, a software screening strategy (Targetscan program, www.targetscan.org) was applied. It was found that only the 3' UTR region of CD133, a transmembrane protein that has been widely used to isolate putative CSC populations in several cancer types, was highly matched as a miR142-3p target. Furthermore, the result of searching the NCI60 tumor database (a dataset of gene expression and miRNA profiles of 60 National Cancer Institute cell lines) and screening for targets whose expression levels were negatively correlated with that of miR142-3p showed that Sox2, a transcriptional factor generally expressed in embryonic stem cell as well as CSCs of several types of tumor, and ADCY9 (AC9), a membrane-bound adenylate cyclase highly expressed in brain, have an opposite expression pattern to miR142-3p, i.e. Sox2 and AC9 were highly expressed in the brain tumor cell lines in the NCI60 database whereas miR142-3p expression was low, compared to other cell lines in the database (FIG. 1E). qRT-PCR analysis of Sox2, AC9 and CD133 mRNA levels in the 70 primary and 30 recurrent GBM patient specimens indicated that the three potential miR142-3p targets were indeed preferentially expressed in the recurrent GBM tissues, while miR142-3p expression was more highly expressed in the primary tissues (FIG. 1F). Notably, statistical analysis of the mRNA expression of these genes in the 7 pairs of primary and recurrent GBM specimens revealed a strong negative correlation between miR142-3p and the three potential targets (FIG. 1G). Collectively, these data indicate that mir142-3p expression is inversely correlated with the levels of Sox2, AC9, CD133, and GBM progression or recurrence.

Example 2

Combined High Expression of Sox2 and AC9 Predicts GBM Patient Prognosis, Survival, and Relapse Since there was an inverse correlation between mir142-3p and Sox2, AC9, CD133, and GBM progression or recurrence, what was next sought was to determine the relationship between expression of these molecules and GBM patient outcome. Expression of Sox2, AC9, CD133 and miR142-3p was examined by immunohistochemical staining and FISH, respectively, in a specimen array panel from the 7 GBM patients (FIG. 2A, one representative case shown in A). Elevated Sox2, AC9 and CD133 expressions were all positively associated with recurrent, poorly differentiated GBM tissues when comparing recurrent (second surgery) with primary (first surgery) GBM specimens (FIGS. 2A, B). In line with previous data, there was also a significant inverse correlation between GBM recurrence and the level of miR142-3p (FIGS. 2A, B). To determine the prognostic significance of Sox2, AC9, CD133 and miR142-3p expression levels, Kaplan-Meier survival analysis of GBM patients was performed according to their expression profile of these genes. The result showed that patients positive for AC9 or Sox2, but not CD133, had a reduced survival rate; whereas patients with high miR142-3p expression had a better survival rate compared with those with low expression of miR142-3p (FIG. 2C; Table 2).

Furthermore, GBM patients who were double-positive for AC9 and Sox2 with low-expression of miR142-3p were predicted to have lower survival rate compared with patients with high miR142-3p level and negative for Sox2 and AC9 expression (p=0.002, FIG. 2D). However, in line with the result in FIG. 2C, CD133 had no effects on GBM patient survival as the presence or absence of CD133 in both Sox2-AC9-miR142-3p$^{high}$ and Sox2$^+$AC9$^+$miR142-3p$^{low}$ patients did not change the survival rate (FIG. 2E; p=0.523: group 1 vs. group 2; p=0.314: group 3 vs. group 4). In the data, CD133 expression was positively associated with GBM relapse (FIGS. 1F and 2B) but not with patient survival (FIGS. 2C and 2E). Collectively, these results suggest that a Sox2$^+$/AC9$^+$/miR142-3p$^{low}$ signature could be a potential predictor for disease progression and clinical outcome of GBM patients (p<0.01; FIGS. 2D and 2E).

Example 3

MiR142-3p Directly Targets the 3' UTR Regions of Sox2, AC9, and CD133

Figure 3:
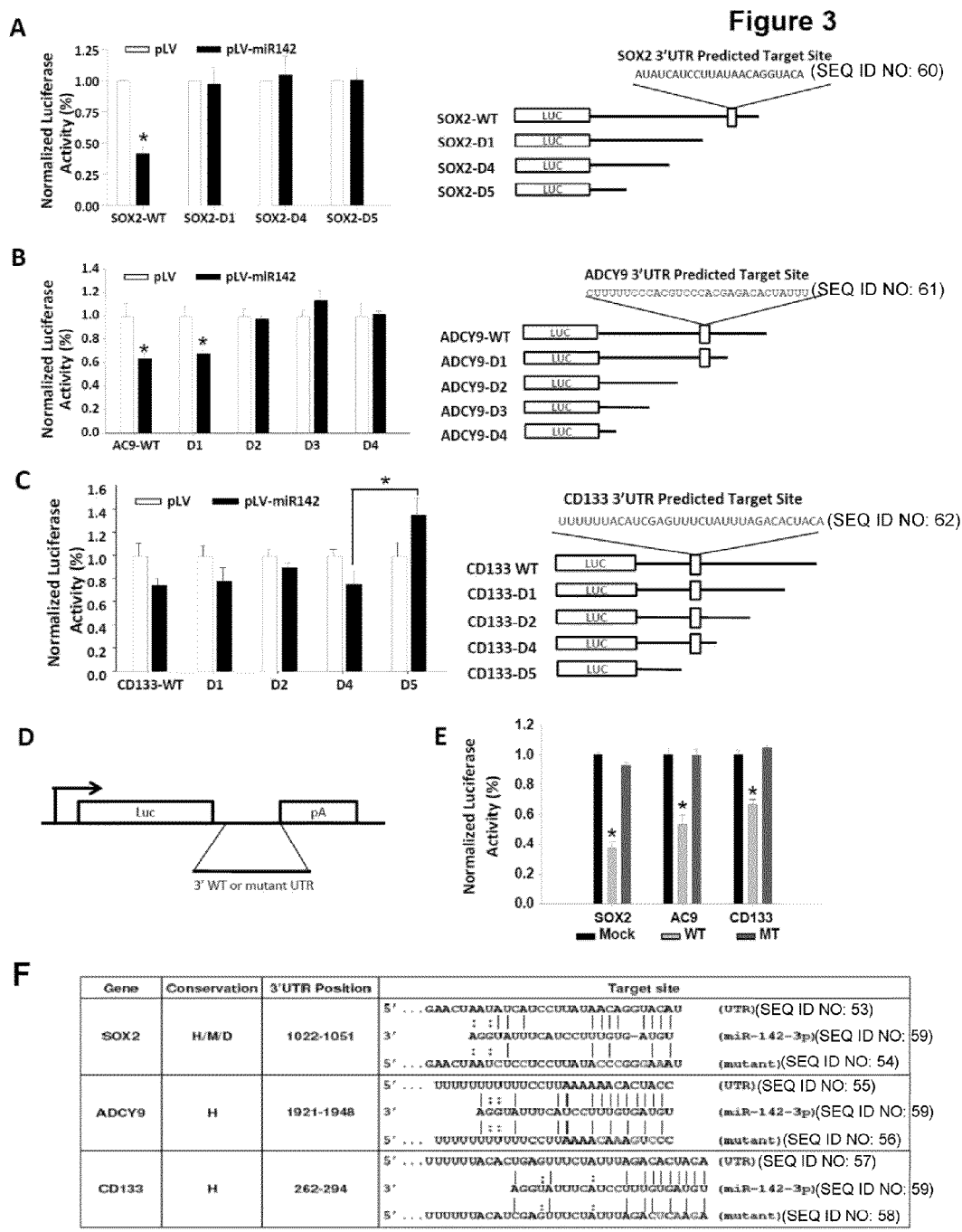
Figure 10:
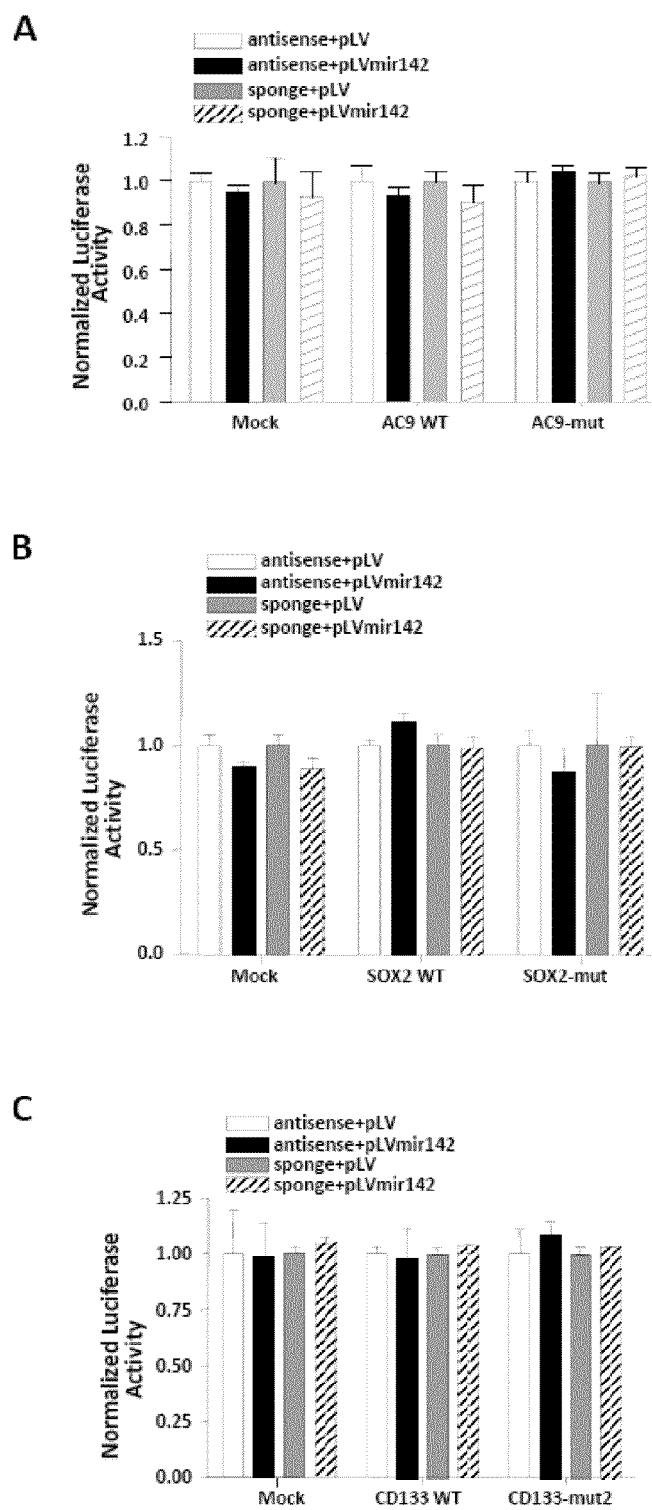

The inverse correlation between miR142-3p and Sox2, AC9, and CD133 prompted the investigation of whether Sox2, AC9 and CD133 are directly targeted by miR142-3p. Luciferase reporter plasmids containing wild-type (WT) (SEQ ID NOS. 60-62) or serial deleted forms (D1-D5) of the 3'UTR regions of Sox2, AC9, and CD133 (FIG. 3A-C, right) were constructed. The luciferase reporter assay was performed by co-transfecting the reporter plasmids with or without miR142-3p in the cultured recurrent GBM cells isolated from patient samples (FIG. 3A-C, left). The results indicated that miR142-3p targeted Sox2 3' UTR near its 3' end (FIG. 3A), and AC9 3' UTR at the region between D1 and D2 (FIG. 3B), though miR142-3p targeting sequence was not identified in both 3'UTR sequence by the Targetscan prediction program (www.targetscan.org). Moreover, as predicted by the Targetscan program, miR142-3p targeted the CD133 3' UTR region, and the region between D4 and D5 was critical for miR142-3p-mediated abolishment of CD133 (p<0.01; FIG. 3D). According to this result, aligned miR142-3p sequence (SEQ ID NO.59) was aligned with the likely region of each 3'UTR, and predicted the miR142-3p targeting region in Sox2, AC9 and CD133 (FIG. 3F). Luciferase reporter plasmids containing wild type (WT) (SEQ ID NOS. 53, 55, 57) or mutated miR142-3p targeting regions (SEQ ID NOS. 54, 56, 58) (FIGS. 3D, F) were then constructed. The reporter assay showed that miR142-3p inhibited the luciferase activity of the wild-type targeting site but not the mutated site (FIG. 3E), implying that the miR142-3p-mediated inhibition of Sox2, AC9 and CD133 is dependent on the identified sequences. To confirm the miR142-3p-dependent inhibition of Sox2, AC9 and CD133, miR142-3p antisense and SPONGE constructs, competitive inhibitors of miRNAs consisting of transcripts containing multiple, tandem binding sites to a miRNA of interest (Ebert et al., 2007), were co-transfected with wild-type or mutated 3'UTR reporters in recurrent GBM cells; the inhibition effects were no longer observed with miR142-3p antisense and SPONGE (FIG. 10). Taken together, these data support that Sox2, AC9 and CD133 are direct inhibitory targets of miR142-3p in recurrent GBM cells.

Example 4

Figure 11:
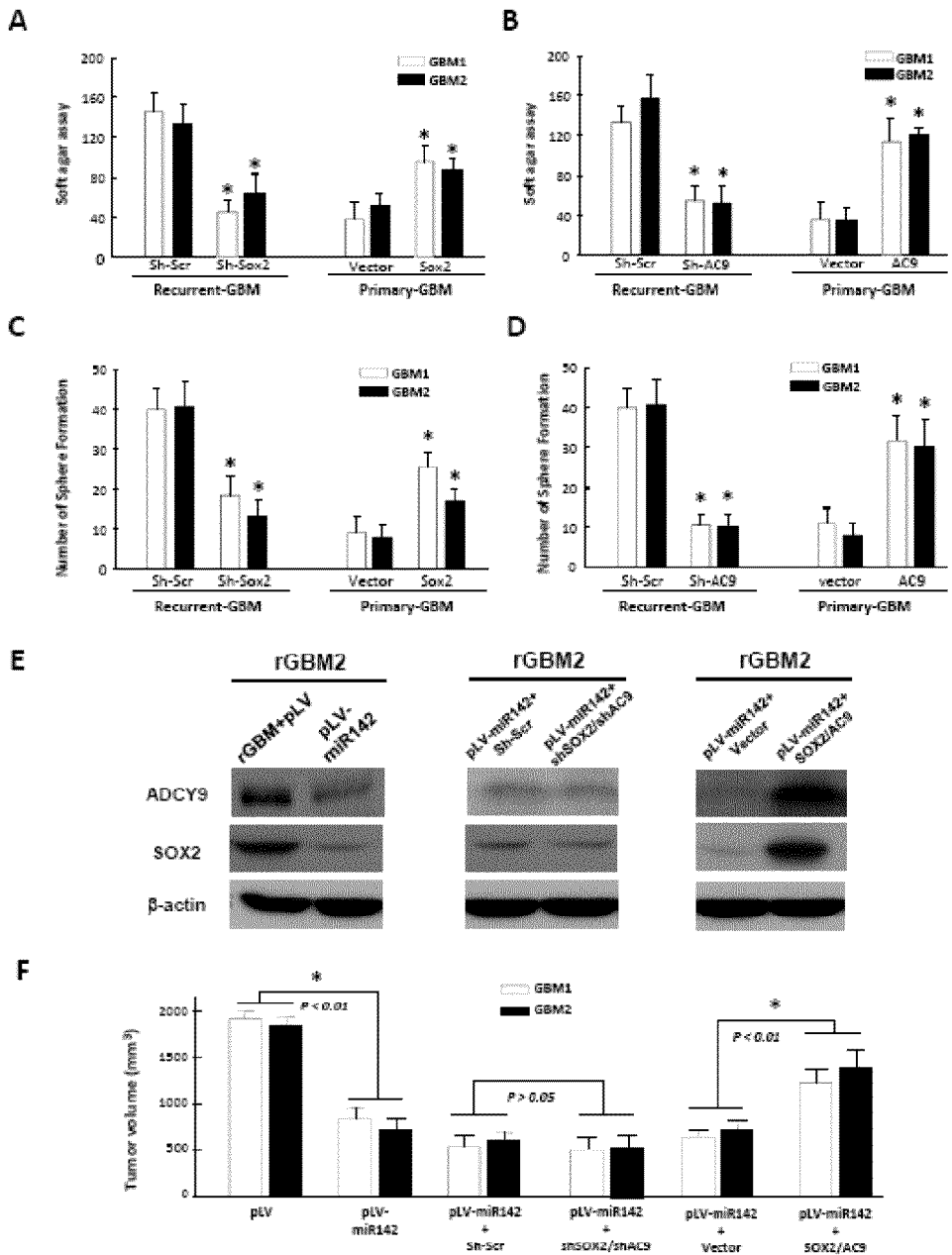
Figure 12:
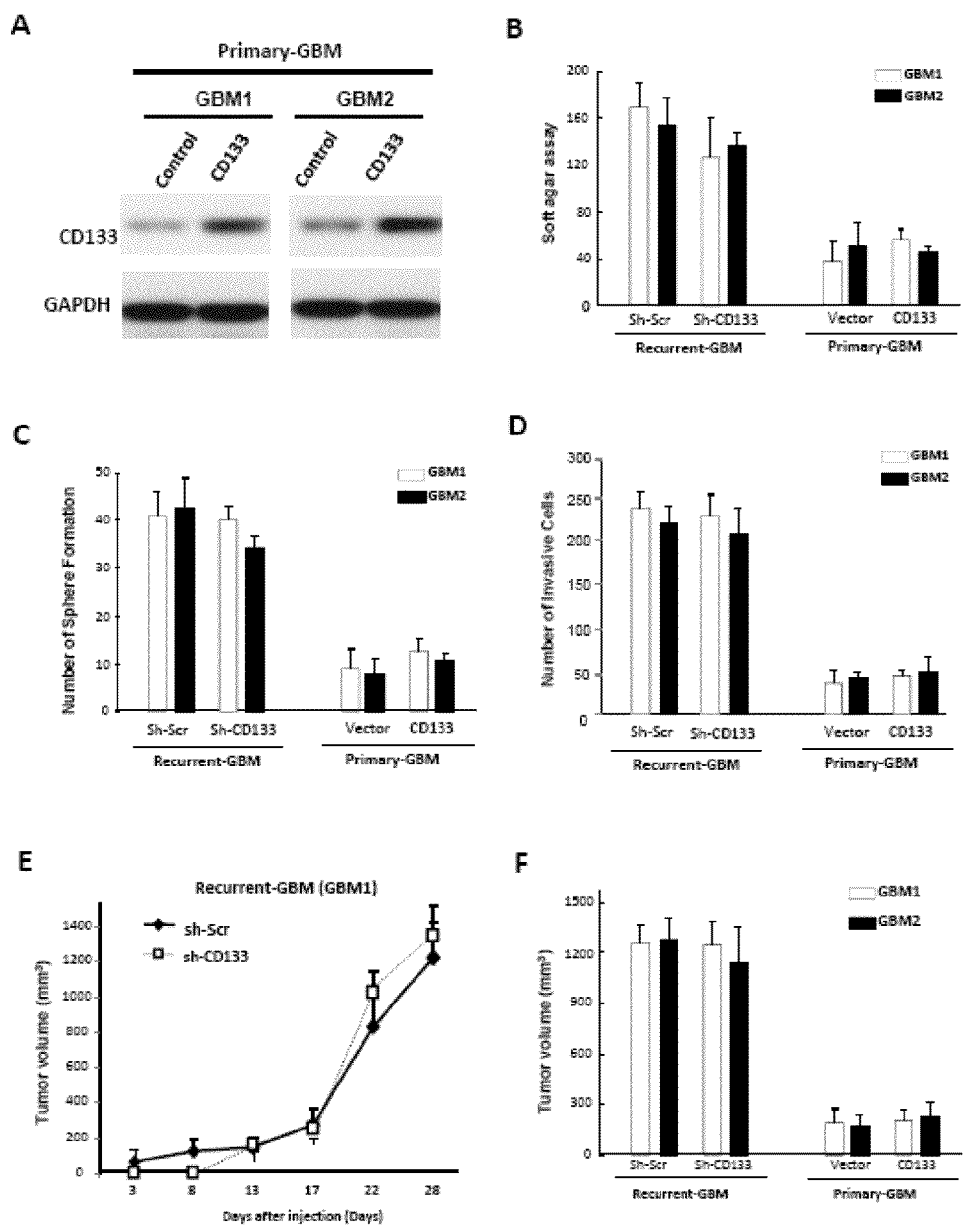

Over-Expression of miR142-3p Inhibited Tumorigenic and Migratory/Invasive Abilities in Recurrent GBM Cells To examine the role of miR142-3p in regulating the aggressive property of recurrent GBMs, miR142-3p was overexpressed by lentivirus infection in recurrent GBM (rGBM) cells from two patients (GBM1 and GBM2). An empty vector-transfected control (rGBM/pLV) was also generated simultaneously. The ectopic miR142-3p expression and the endogenous Sox2, AC9 and CD133 protein levels of these cell lines was validated by northern (FIG. 4A, bottom 2 blots) and Western blot (FIG. 4A, top 4 blots), respectively. Functional analysis on these cell lines showed that both miR142-3p-overexpressed rGBM (rGBM/miR142-3p) cell lines had reduced sphere formation ability (FIG. 4B), less soft agar colony number (FIG. 4C), and inhibited migration and invasion capacity (FIG. 4D), compared with their parental rGBM and control rGBM/pLV cells. It was further investigated that the involvement of Sox2, AC9 and CD133 in miR142-3p-mediated regulation of tumorigenic property in rGBMs. Using shRNA-mediated gene silencing, Sox2, AC9, or CD133 in rGBM cells derived from GBM1 and GBM2 specimens were specifically knocked-down (FIG. 4E), and subjected them to in vitro functional analysis and in vivo tumor formation assay. Similar to the effects of miR142-3p overexpression, the results of the knock-down study showed that the invasion tendency (FIG. 4F), anchorage independence (FIG. 11A-B), sphere formation ability (FIG. 11C-D) and in vivo tumorigenicity (FIG. 4G) of rGBM cells were significantly suppressed by shRNAs against Sox2 or AC9, but not CD133 (FIG. 4F-G, comparing shSox2, shAC9, and shCD133 with shScr; FIG. 12). To determine if miR142-3p-mediated down-regulation of Sox2 and AC9 is indeed the reason for the inhibition of miR142-3p's suppressive effects, Sox2 and AC9 in the rGBM/miR142-3p cells were re-expressed (FIG. 11E), which resulted in enhanced tumorigenicity (FIG. 11F). As expected, Sox2/AC9 double knocked-down had little effect in this experiment (FIG. 11F) as Sox2 and AC9 expression was already low in this cell line (FIG. 11E, middle) due to the presence of miR142-3p. It was conclude that miR142-3p- and Sox2/AC9-mediated rGBM tumorigenicity are concurrent events and that miR142-3p overexpression reduced the tumor aggressive characters in rGBM partially, if not all, through inhibiting Sox2 and AC9.

Example 5

Figure 13:
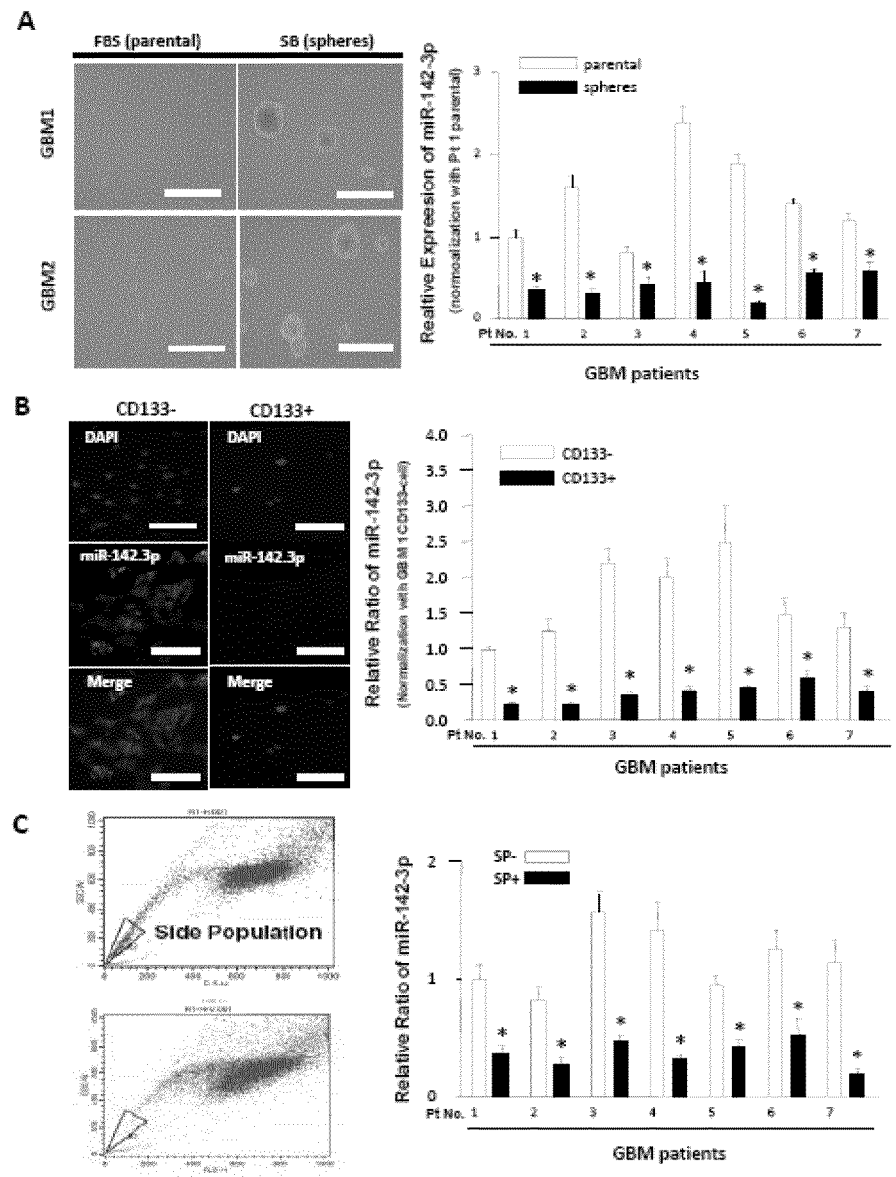
Figure 14:
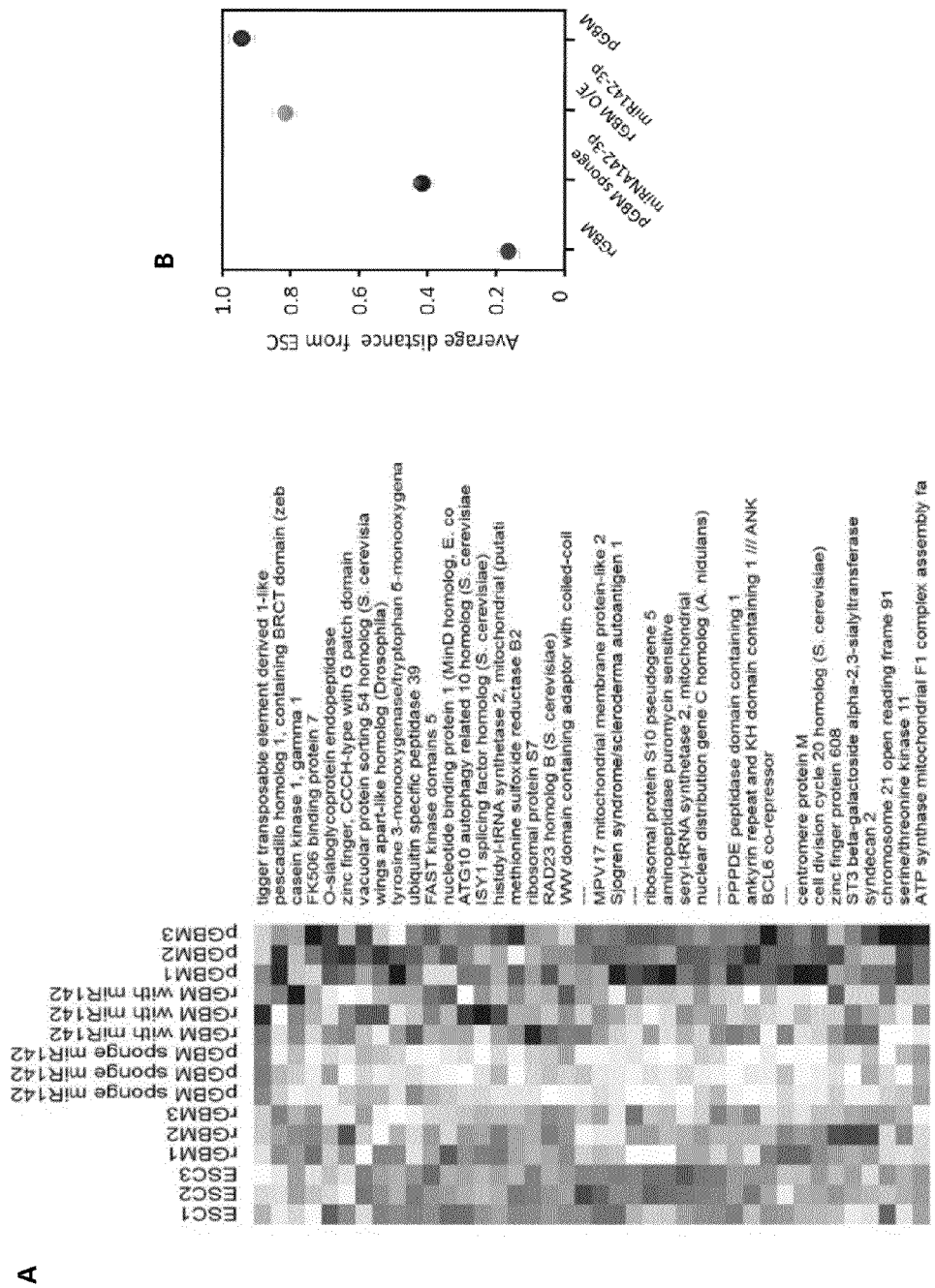

MiR142-3p Depletion Promoted Cancer Stem-Like and Tumor-Initiating Capability in Primary GBM Recent reports suggest that recurrent GBMs possess the potential of cancer stem cell (CSC)-like properties, and presents characteristics of aggressive tumor. Based on these studies as well as the finding according to the present invention that miR142-3p is low in recurrent GBM but high in primary GBM, the relationship between miR142-3p and cancer stemness properties of GBM were further explored. Endogenous miR142-3p was knocked down in the primary GBM (pGBM) cells isolated from the same 2 patients as described previously (GBM1 and GBM2) using the miRNA SPONGE (Spg) strategy. Endogenous Sox2, AC9 and CD133 protein expressions were higher in miR142-3p-knocked down primary GBM (pGBM/Spg) cells than in parental pGBM and control (pGBM/Scr) cells (FIG. 5A). Next, self-renewal and tumorigenic properties of pGBM/Spg cells were assessed by the spheroid formation and colony formation assays; both abilities were significantly higher in pGBM/Spg than in parental or control cells (p<0.05; FIG. 5B). It was also examined that the successful sphere formation over serial passages of culture, a key behavior for evaluating the persistent self-renewal property of CSCs, and showed that the self-renewal capacity of all pGBM/Spg cells established from three primary GBM patient specimens (GBM1-3) is conserved for several passages of culture (FIG. 5C). Moreover, migratory/invasion abilities were also significantly greater in pGBM/Spg than in pGBM or pGBM/Scr cells (p<0.05; FIG. 5D), and miR142-3p knockdown in pGBM was also found concurrent with increased number of cells in the side population (p<0.05; FIG. 5E), for which CSCs has been suggested to contribute to. The role of miR142-3p in regulating GBM-CSCs is further supported by the fact that miR142-3p level was high in non-CSC GBM cells but low in GBM-CSCs. CSC-like GBM cells were isolated from 7 GBM patient specimens according to their spheroid body formation ability, CD133 surface marker expression, and side population identification (FIG. 13). All isolated GBM-CSCs from the 7 patients, exhibited low expression of miR142-3p. In addition, bioinformatics analysis on transcriptome signature suggested that suppression of miR142-3p in pGBM promoted a signature shift toward that of mesenchymal stem cell (MSC) and embryonic stem cell (ESC; FIG. 5F and FIG. 14).

It was next determined whether miR142-3P downregulation increased tumor initiating activity of pGBM in vivo. Compared to scrambled SPONGE transfected control, in xenotransplanted non-SCID mice, it was found that silencing endogenous miR142-3p increased the tumor forming ability of primary GBM cells (FIG. 5G, GFP signal represented tumor locus). The data showed that SPONGE-miR142-3p increased the in vivo tumor-initiating ability by 10 to 10,000 fold in the pGBM cells isolated from six GBM patients (FIG. 5H; FIG. 15). The pGBM cells from patient No. 8 were unable to form tumors when injected into the brain striatum of NOD-SCID mice with a number of cells as large as 500,000 (FIG. 5H, parental). However, with knock-down of miR142-3p by SPONGE, as few as 50 injected cells were capable to regenerate a new tumor in one of three transplanted NOD-SCID mice, and with 1000 injected cells all three mice were able to form new tumors (FIG. 5H, miR142-3p SPONGE). This evidence supports that down-regulation of miR142-3p in pGBM renders stem-like properties to initiate and regenerate new tumors. Overall, maintaining miR142-3p at a low expression level is crucial for GBM cells to retain the CSC properties and in vivo tumor-initiating activity.

Example 6

Mesenchymal Transformation is Maintained by Suppression Of MiR142-3p or Enhanced Expression of Sox2/AC9

Figure 6:
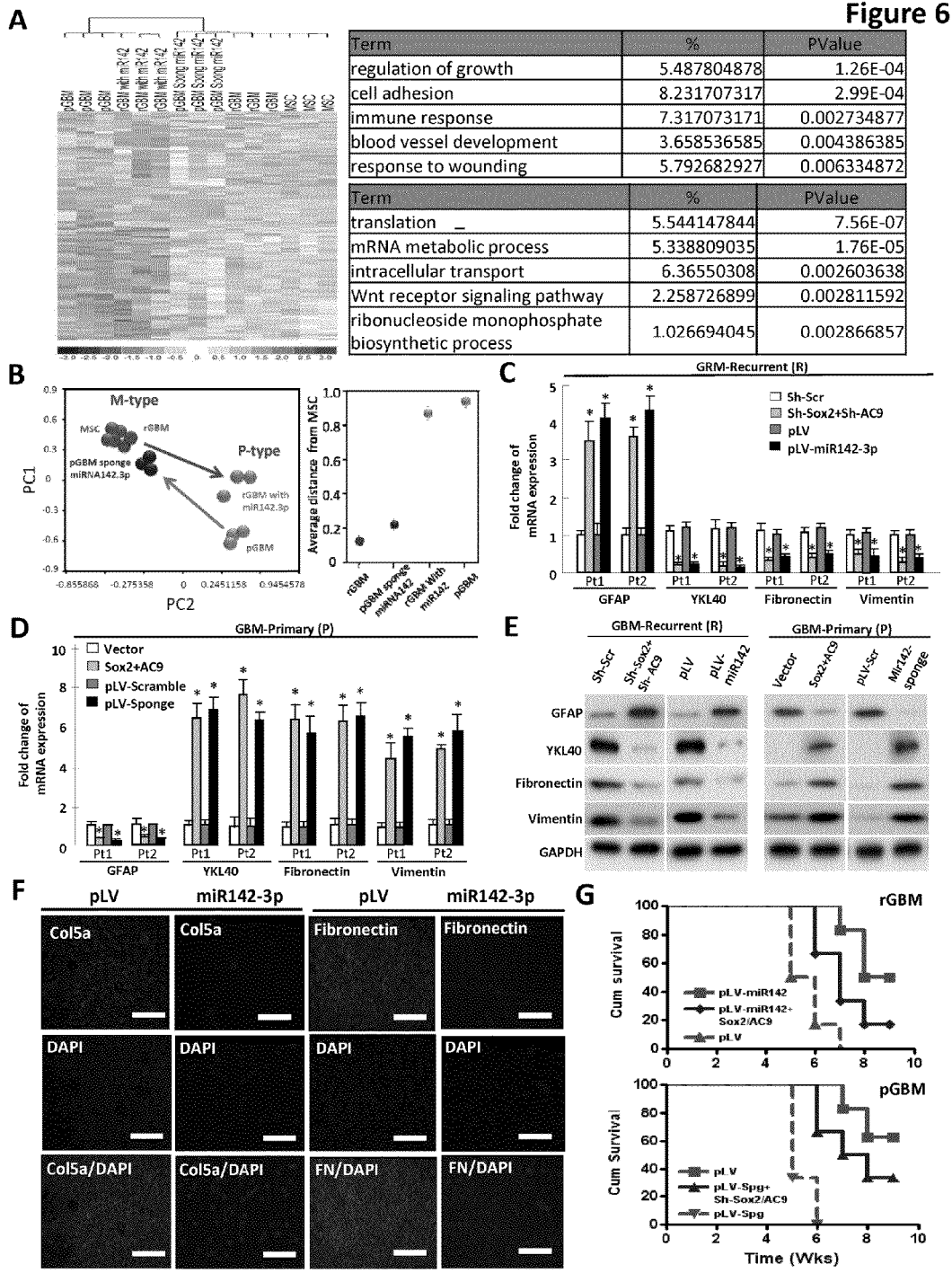

Recurrent GBM cells have been shown to have more invasive and mesenchymal properties than primary GBM cells. Carro et al. (2010) demonstrated that a glioma-specific regulatory network involves a transcriptional module that activates mesenchymal gene expression in malignant glioma. To explore whether miR142-3p governs mesenchymal transformation in GBM, transcriptome profiling using microarray analysis was performed. The results of bioinformatics analysis showed that overexpressed miR142-3p in rGBM cells reduced mesenchymal and induced neuronal transcriptomes, while silencing of miR142-3p in pGBM induced mesenchymal transcriptomes (FIG. 6A). In line with this data, multidimensional scaling (MDS) analysis revealed that miR142-3p-knock down reprogrammed pGBM cells toward a mesenchymal signature, whereas miR142-3p overexpression in rGBM diverted it from mesenchymal but toward pro-neuronal signature (FIG. 6B). The data supported that the presence or absence of miR142-3p determines GBM cells characteristics in terms of stemness signature.

To determine the involvement of Sox2 and AC9 in the miR142-3p-dependent mesenchymal transformation, a panel of mesenchymal-favored markers (YKL40 (also known as CHI3L1), fibronectin, and vimentin) and glial fibrillary acidic protein (GFAP, a specific glial-lineage marker) (Carro et al., 2010) were compared. With Sox2/AC-9 double knockdown or miR142-3p overexpression in rGBM cells, YKL40, fibronectin, and vimentin transcripts were decreased, while GFAP transcript was increased (FIGS. 6C, E). Contrarily, Sox2/AC9 overexpression or miR142-3p silencing in pGBM resulted in repressed GFAP but elevated mesenchymal-favored markers (FIGS. 6D, E). Notably, the miR142-3p-mediated suppression of mesenchymal-favored markers in rGBM cells was enhanced by additional co-overexpression of Sox2/AC9, and vice versa (FIG. 16A). Using an immunofluorecence staining, decreased expression levels of collagen 5a (Col5a, a mesenchymal marker of GBM) and fibronectin were also shown in the xenograft tumor derived from rGBM/miR142-3p-transplanted immunocompromised mice (FIG. 6F), and Sox2/AC9 overexpression restored the expression of Col5a and fibronectin (data not shown). The role of miR142-3p-Sox2/AC9 regulatory mechanism in mesenchymal transformation was further supported by the wound-healing migration assay, in which the miR142-3p-dependent suppression of rGBM motility was rescued by the co-overexpressed Sox2/AC9, while the miR142-3p SPONGE-mediated enhanced motility of pGBM was repressed by double knockdown of Sox2/AC9 (FIG. 16B-C). Moreover, cumulative survival analysis indicated that rGBM/miR142-3p-transplanted immunocompromised mice had increased survival rate in comparison to parental rGBM-transplanted mice; with additional Sox2/AC9 co-overexpression, the survival rate was decreased (FIG. 6G, top). On the contrary, the miR142-3p SPONGE-mediated decrease of pGBM survival rate was rescued by further double knock down of Sox2/AC9 (FIG. 6G, bottom). Collectively, these results suggest that the miR142-3p-dependent mesenchymal transformation of GBM cells may be mediated through Sox2 and AC9 partially, if not all.

Example 7

Down-Regulating miR142-3p Increased the Ionizing-Radiation Resistance in Radiosensitive Primary GBM The property of resistance to irradiation treatment is the one of the major clinical criterion to characterize cancer stem cells (CSCs) in malignant glioma (Bao et al., 2006). The role of miR142-3p in regulating the radiosensivity in GBMs was therefore evaluated. To determine the radiosensitivity, an ionizing radiation (IR) dose from 0 to 10 Gy was used to treat recurrent GBM with or without overexpressed miR142-3p. As shown in FIG. 7A, after IR treatment, the numbers of surviving rGBM cells without miR142-3p overexpresion (rGBM/pLV and parental rGBM cells) were significantly higher than those of rGBM/miR142-3p (P<0.01; FIG. 7A). In contrast, primary GBM cells with SPONGE miR142-3p had better survival rate and also possessed a higher degree of radioresistance as compared with the parental and vector control (FIG. 7B). To further validate the radiosensitizing effect of miR142-3p in rGBM tumor-bearing immunocompromised mice, rGBM/miR142-3p and rGBM/pLV-injected mice were treated with 4 Gy IR and the tumor size was assessed by GFP-positive region (FIG. 7C). The result showed that miR142-3p reduced tumor size after radiation treatment, compared with rGBM/pLV tumor. rGBM/pLV tumor- or rGBM/miR142-3p tumor-bearing mice were treated with or without IR, and the tumor growth was monitored for 6 weeks (FIG. 7D). rGBM cells formed a large brain tumor 6 weeks after transplantation (rGBM/pLV); and the IR treatment had limited inhibitory effect on tumor growth (rGBM/pLV/IR). On the contrary, miR142-3p overexpression dramatically repressed tumor growth (rGBM/miR142-3p); and with additional IR treatment, the size of tumor was maintained in a merely detectable level (rGBM/miR142-3p/IR). This result not only confirmed the inhibitory role of miR142-3p on tumor growth, but also presented a synergetic effect of miR142-3p and IR treatments. Furthermore, to investigate the involvement of Sox2 and AC9 in the miR142-3p-mediated radiosensitivity, mice transplanted with pGBM/Scr, pGBM/Spg, or pGBM/Spg+shSox2/shAC9 cells were treated with or without IR and monitored by MRI imaging (FIG. 7E-F). The result showed that silencing of endogenous miR142-3p (pGBM/Spg) significantly promoted tumor growth even with the IR treatment, compared with the radiosensitive control pGBM/Scr cells (FIG. 7F). With additional double knockdown of Sox2 and AC9 (pGBM/Spg/shSox2+shAC9), the radiosensitivity of pGBM/Spg was increased. Moreover, the rescue effect of double knockdown Sox2 and AC9 on radiosensitivity was also observed in the in vivo tumor-initiating ability of pGBM (FIG. 7G). The miR142-3p-SPONGE-mediated elevation of tumor-initiation capacity in pGBM cells was repressed by Sox2/AC9 double knockdown, and this repression was even more dramatic with IR treatment. Collectively, these data indicated that miR142-3p sensitizes GBM cells to IR, in which Sox2 and AC9 are involved.

Example 8

Orthotopical Delivery of miR142-3p in rGBM-Transplanted Mice Attenuated the Tumorigenicity and Mesencymal Aggressiveness and Restored the Radiosensitivity Previously, miRNA gene delivery by adenovirus vectors or injection of miRNAs constructed with locked nucleic acid (LNA)- or phosphothiolatediester-modified backbones were shown a promising suppression on tumor progression (Patrick et al., 2010; Zhang et al., 2010). The therapeutic potential of LNA-modified miR142-3p oligonucleotides in repressing recurrent GBM tumors was therefore examined (FIG. 8A). rGBM-GFP cells were injected into the stratum of mice brain 5 days before LNA-modified mutated or wild-type miR-142-3p (Mut LNA-miR142-3p and LNA-miR142-3p, respectively) injections into the tumor locus. Compared with rGBM-GFP tumors injected with Mut LNA-miR142-3p, LNA-miR142-3p reduced tumor volumes according to the GFP imaging (FIG. 8A); and the inhibition effect of LNA-miR142-3p on tumor size were observed in both rGBM tumors derived from GBM1 and GBM2 (FIG. 8B). To determine whether tumor shrinkage was caused by transformation into other glioma cell types, sectioned brain tumor samples removed from mice treated with Mut LNA-miR142-3p or LNA-miR142-3p were stained and showed reduced vimentin and fibronectin expressions in LNA-miR142-3p treated tumor (FIG. 8C). This pathological examination suggests that LNA-miR142-3p injection reduced the mesenchymal properties of rGBM tumors. Furthermore, the expression levels of mesenchymal markers (YKL40, nestin, fibronectin (FN), vimentin (VM)) and stemness genes (Oct4, Sox2, Nanog, Klf4) were significantly suppressed in the LNA-miR142-3p treated rGBM tumor (FIG. 8D). The radiosensitizing effect of LNA-miR142-3p in vivo was next examined; significant reduction of rGBM tumor volume was observed upon LNA-miR142-3p plus IR treatment, compared with Mut LNA-miR142-3p plus IR-treated tumor. (FIG. 8E). Notably, though LNA-miR142-3p alone appears to be a tumor repressor (*$p<0.05$; FIG. 8E, white bars in right panel), the synergetic effect of LNA-miR142-3p and IR repressed the tumor volume further severe (#$p<0.05$; FIG. 8E. right). Taken together, liposome-encapsulated LNA-modified miR142-3p oligonucleotides injection transformed intracranial rGBM cells into less malignant glioma cells, greatly reduced the mesenchymal properties and significantly improved radiosensitivity.

REFERENCES

Bao, S., Wu, Q., McLendon, R. E., Hao, Y., Shi, Q., Hjelmeland, A. B., Dewhirst, M. W., Bigner, D. D., and Rich, J. N. (2006). Glioma stem cells promote radioresistance by preferential activation of the DNA damage response. Nature 444, 756-760.

Beier, D., Hau, P., Proescholdt, M., Lohmeier, A., Wischhusen, J., Oefner, P. J., Aigner, L., Brawanski, A., Bogdahn, U., and Beier, C. P. (2007). CD133(+) and CD133(−) glioblastoma-derived cancer stem cells show differential growth characteristics and molecular profiles. Cancer Res 67, 4010-4015.

Carro, M. S., Lim, W. K., Alvarez, M. J., Bollo, R. J., Zhao, X., Snyder, E. Y., Sulman, E. P., Anne, S. L., Doetsch, F., Colman, H., et al. (2010). The transcriptional network for mesenchymal transformation of brain tumours. Nature 463, 318-325.

Chan, J. A., Krichevsky, A. M., and Kosik, K. S. (2005). MicroRNA-21 is an antiapoptotic factor in human glioblastoma cells. Cancer Res 65, 6029-6033.

Chen, C. Z., Li, L., Lodish, H. F., and Bartel, D. P. (2004). MicroRNAs modulate hematopoietic lineage differentiation. Science 303, 83-86.

Chen, R., Nishimura, M. C., Bumbaca, S. M., Kharbanda, S., Forrest, W. F., Kasman, I. M., Greve, J. M., Soriano, R. H., Gilmour, L. L., Rivers, C. S., et al. (2010). A hierarchy of self-renewing tumor-initiating cell types in glioblastoma. Cancer Cell 17, 362-375.

Chen, Y. C., Hsu, H. S., Chen, Y. W., Tsai, T. H., How, C. K., Wang, C. Y., Hung, S. C., Chang, Y. L., Tsai, M. L., Lee, Y. Y., et al. (2008). Oct-4 expression maintained cancer stem-like properties in lung cancer-derived CD133-positive cells. PLoS ONE 3, e2637.

Chiou, S. H., Kao, C. L., Lin, H. T., Tseng, W. S., Liu, R. S., Chung, C. F., Ku, H. H., Lin, C. P., and Wong, T. T. (2006). Monitoring the growth effect of xenotransplanted human medulloblastoma in an immunocompromised mouse model using in vitro and ex vivo green fluorescent protein imaging. Childs Nery Syst 22, 475-480.

Corbeil, D., Roper, K., Hellwig, A., Tavian, M., Miraglia, S., Watt, S. M., Simmons, P. J., Peault, B., Buck, D. W., and Huttner, W. B. (2000). The human AC133 hematopoietic stem cell antigen is also expressed in epithelial cells and targeted to plasma membrane protrusions. J Biol Chem 275, 5512-5520.

Croce, C. M. (2009). Causes and consequences of microRNA dysregulation in cancer. Nat Rev Genet 10, 704-714.

Decarvalho, A. C., Nelson, K., Lemke, N., Lehman, N. L., Arbab, A. S., Kalkanis, S., and Mikkelsen, T. Gliosarcoma stem cells undergo glial and mesenchymal differentiation in vivo. Stem Cells 28, 181-190.

Dehdashti, A. R., Hegi, M. E., Regli, L., Pica, A., and Stupp, R. (2006). New trends in the medical management of glioblastoma multiforme: the role of temozolomide chemotherapy. Neurosurg Focus 20, E6.

Diehn, M., Cho, R. W., Lobo, N. A., Kalisky, T., Dorie, M. J., Kulp, A. N., Qian, D., Lam, J. S., Ailles, L. E., Wong, M., et al. (2009). Association of reactive oxygen species levels and radioresistance in cancer stem cells. Nature 458, 780-783.

Ebert, M. S., Neilson, J. R., and Sharp, P. A. (2007). MicroRNA sponges: competitive inhibitors of small RNAs in mammalian cells. Nat Methods 4, 721-726.

Ferretti, E., De Smaele, E., Miele, E., Laneve, P., Po, A., Pelloni, M., Paganelli, A., Di Marcotullio, L., Caffarelli, E., Screpanti, I., et al. (2008). Concerted microRNA control of Hedgehog signalling in cerebellar neuronal progenitor and tumour cells. EMBO J 27, 2616-2627.

Gangemi, R. M., Griffero, F., Marubbi, D., Perera, M., Capra, M. C., Malatesta, P., Ravetti, G. L., Zona, G. L., Daga, A., and Corte, G. (2009). SOX2 silencing in glioblastoma tumor-initiating cells causes stop of proliferation and loss of tumorigenicity. Stem Cells 27, 40-48.

Garzia, L., Andolfo, I., Cusanelli, E., Marino, N., Petrosino, G., De Martino, D., Esposito, V., Galeone, A., Navas, L., Esposito, S., et al. (2009). MicroRNA-199b-5p impairs cancer stem cells through negative regulation of HES1 in medulloblastoma. PLoS One 4, e4998.

Gauwerky, C. E., Huebner, K., Isobe, M., Nowell, P. C., and Croce, C. M. (1989). Activation of MYC in a masked t(8;17) translocation results in an aggressive B-cell leukemia. Proc Natl Acad Sci USA 86, 8867-8871.

Gillies, J. K., and Lorimer, I. A. (2007). Regulation of p27Kip1 by miRNA 221/222 in glioblastoma. Cell Cycle 6, 2005-2009.

Hilbe, W., Dirnhofer, S., Oberwasserlechner, F., Schmid, T., Gunsilius, E., Hilbe, G., Woll, E., and Kahler, C. M. (2004). CD133 positive endothelial progenitor cells contribute to the tumour vasculature in non-small cell lung cancer. J Clin Pathol 57, 965-969.

Huang, B., Zhao, J., Lei, Z., Shen, S., Li, D., Shen, G. X., Zhang, G. M., and Feng, Z. H. (2009). miR-142-3p restricts cAMP production in CD4+CD25− T cells and CD4+CD25+ TREG cells by targeting AC9 mRNA. EMBO Rep 10, 180-185.

Huse, J. T., Brennan, C., Hambardzumyan, D., Wee, B., Pena, J., Rouhanifard, S. H., Sohn-Lee, C., le Sage, C., Agami, R., Tuschl, T., and Holland, E. C. (2009). The PTEN-regulating microRNA miR-26a is amplified in high-grade glioma and facilitates gliomagenesis in vivo. Genes Dev 23, 1327-1337.

Iliopoulos, D., Lindahl-Allen, M., Polytarchou, C., Hirsch, H. A., Tsichlis, P. N., and Struhl, K. (2010). Loss of miR-200 inhibition of Suz12 leads to polycomb-mediated repression required for the formation and maintenance of cancer stem cells. Mol Cell 39, 761-772.

Ji, J., Yamashita, T., Budhu, A., Forgues, M., Jia, H. L., Li, C., Deng, C., Wauthier, E., Reid, L. M., Ye, Q. H., et al. (2009a). Identification of microRNA-181 by genome-wide screening as a critical player in EpCAM-positive hepatic cancer stem cells. Hepatology 50, 472-480.

Ji, Q., Hao, X., Zhang, M., Tang, W., Yang, M., Li, L., Xiang, D., Desano, J. T., Bommer, G. T., Fan, D., et al. (2009b). MicroRNA miR-34 inhibits human pancreatic cancer tumor-initiating cells. PLoS One 4, e6816.

Joo, K. M., Kim, S. Y., Jin, X., Song, S. Y., Kong, D. S., Lee, J. I., Jeon, J. W., Kim, M. H., Kang, B. G., Jung, Y., et al. (2008). Clinical and biological implications of CD133-positive and CD133-negative cells in glioblastomas. Lab Invest 88, 808-815. Kefas, B., Godlewski, J., Comeau, L., Li, Y., Abounader, R., Hawkinson, M., Lee, J., Fine, H., Chiocca, E. A., Lawler, S., and Purow, B. (2008). microRNA-7 inhibits the epidermal growth factor receptor and the Akt pathway and is down-regulated in glioblastoma. Cancer Res 68, 3566-3572.

Li, T., Li, D., Sha, J., Sun, P., and Huang, Y. (2009). MicroRNA-21 directly targets MARCKS and promotes apoptosis resistance and invasion in prostate cancer cells. Biochem Biophys Res Commun 383, 280-285.

Malzkorn, B., Wolter, M., Liesenberg, F., Grzendowski, M., Stuhler, K., Meyer, H. E., and Reifenberger, G. (2009). Identification and Functional Characterization of microRNAs Involved in the Malignant Progression of Gliomas. Brain Pathol.

Ogden, A. T., Waziri, A. E., Lochhead, R. A., Fusco, D., Lopez, K., Ellis, J. A., Kang, J., Assanah, M., McKhann, G. M., Sisti, M. B., et al. (2008). Identification of A2B5+CD133− tumor-initiating cells in adult human gliomas. Neurosurgery 62, 505-514; discussion 514-505.

Pallini, R., Ricci-Vitiani, L., Montano, N., Mollinari, C., Biffoni, M., Cenci, T., Pierconti, F., Martini, M., De Maria, R., and Larocca, L. M. (2010). Expression of the stem cell marker CD133 in recurrent glioblastoma and its value for prognosis. Cancer.

Patrick, D. M., Montgomery, R. L., Qi, X., Obad, S., Kauppinen, S., Hill, J. A., van Rooij, E., and Olson, E. N. (2010). Stress-dependent cardiac remodeling occurs in the absence of microRNA-21 in mice. J Clin Invest 120, 3912-3916.

Riggi, N., Suva, M. L., De Vito, C., Provero, P., Stehle, J. C., Baumer, K., Cironi, L., Janiszewska, M., Petricevic, T., Suva, D., et al. EWS-FLI-1 modulates miRNA145 and SOX2 expression to initiate mesenchymal stem cell reprogramming toward Ewing sarcoma cancer stem cells. Genes Dev 24, 916-932.

Sasayama, T., Nishihara, M., Kondoh, T., Hosoda, K., and Kohmura, E. (2009). MicroRNA-10b is overexpressed in malignant glioma and associated with tumor invasive factors, uPAR and RhoC. Int J Cancer 125, 1407-1413.

Shimono, Y., Zabala, M., Cho, R. W., Lobo, N., Dalerba, P., Qian, D., Diehn, M., Liu, H., Panula, S. P., Chiao, E., et al. (2009). Downregulation of miRNA-200c links breast cancer stem cells with normal stem cells. Cell 138, 592-603.

Silahtaroglu, A. N., Nolting, D., Dyrskjot, L., Berezikov, E., Moller, M., Tommerup, N., and Kauppinen, S. (2007). Detection of microRNAs in frozen tissue sections by fluorescence in situ hybridization using locked nucleic acid probes and tyramide signal amplification. Nat Protoc 2, 2520-2528.

Silber, J., Lim, D. A., Petritsch, C., Persson, A. I., Maunakea, A. K., Yu, M., Vandenberg, S. R., Ginzinger, D. G., James, C. D., Costello, J. F., et al. (2008). miR-124 and miR-137 inhibit proliferation of glioblastoma multiforme cells and induce differentiation of brain tumor stem cells. BMC Med 6, 14.

Stupp, R., Hegi, M. E., Gilbert, M. R., and Chakravarti, A. (2007). Chemoradiotherapy in malignant glioma: standard of care and future directions. J Clin Oncol 25, 4127-4136.

Stupp, R., Mason, W. P., van den Bent, M. J., Weller, M., Fisher, B., Taphoorn, M. J., Belanger, K., Brandes, A. A., Marosi, C., Bogdahn, U., et al. (2005). Radiotherapy plus concomitant and adjuvant temozolomide for glioblastoma. N Engl J Med 352, 987-996.

Sun, W., Shen, W., Yang, S., Hu, F., Li, H., and Zhu, T. H. (2010). miR-223 and miR-142 attenuate hematopoietic cell proliferation, and miR-223 positively regulates miR-142 through LMO2 isoforms and CEBP-beta. Cell Res 20, 1158-1169.

Sutter, R., Shakhova, O., Bhagat, H., Behesti, H., Sutter, C., Penkar, S., Santuccione, A., Bernays, R., Heppner, F. L., Schuller, U., et al. Cerebellar stem cells act as medulloblastoma-initiating cells in a mouse model and a neural stem cell signature characterizes a subset of human medulloblastomas. Oncogene 29, 1845-1856.

Sutter, R., Shakhova, O., Bhagat, H., Behesti, H., Sutter, C., Penkar, S., Santuccione, A., Bernays, R., Heppner, F. L., Schuller, U., et al. (2010). Cerebellar stem cells act as medulloblastoma-initiating cells in a mouse model and a neural stem cell signature characterizes a subset of human medulloblastomas. Oncogene 29, 1845-1856.

Verhaak, R. G., Hoadley, K. A., Purdom, E., Wang, V., Qi, Y., Wilkerson, M. D., Miller, C. R., Ding, L., Golub, T., Mesirov, J. P., et al. Integrated genomic analysis identifies clinically relevant subtypes of glioblastoma characterized by abnormalities in PDGFRA, IDH1, EGFR, and NFL Cancer Cell 17, 98-110.

Wang, J., Sakariassen, P. O., Tsinkalovsky, O., Immervoll, H., Boe, S. O., Svendsen, A., Prestegarden, L., Rosland, G., Thorsen, F., Stuhr, L., et al. (2008). CD133 negative glioma cells form tumors in nude rats and give rise to CD133 positive cells. Int J Cancer 122, 761-768.

Xu, N., Papagiannakopoulos, T., Pan, G., Thomson, J. A., and Kosik, K. S. (2009). MicroRNA-145 regulates OCT4, SOX2, and KLF4 and represses pluripotency in human embryonic stem cells. Cell 137, 647-658.

Yu, F., Deng, H., Yao, H., Liu, Q., Su, F., and Song, E. (2010). Mir-30 reduction maintains self-renewal and inhibits apoptosis in breast tumor-initiating cells. Oncogene 29, 4194-4204.

Yuan, W., Sun, W., Yang, S., Du, J., Zhai, C. L., Wang, Z. Q., Zhang, J., and Zhu, T. H. (2008). Downregulation of microRNA-142 by proto-oncogene LMO2 and its co-factors. Leukemia 22, 1067-1071.

Zeppernick, F., Ahmadi, R., Campos, B., Dictus, C., Helmke, B. M., Becker, N., Lichter, P., Unterberg, A., Radlwimmer, B., and Herold-Mende, C. C. (2008). Stem cell marker CD133 affects clinical outcome in glioma patients. Clin Cancer Res 14, 123-129.

Zhang, Y., Qu, Z., Kim, S., Shi, V., Liao, B., Kraft, P., Bandaru, R., Wu, Y., Greenberger, L. M., and Horak, I. D. (2010). Down-modulation of cancer targets using locked nucleic acid (LNA)-based antisense oligonucleotides without transfection. Gene Ther.

Zhao, S., Lin, Y., Xu, W., Jiang, W., Zha, Z., Wang, P., Yu, W., Li, Z., Gong, L., Peng, Y., et al. (2009). Glioma-derived mutations in IDH1 dominantly inhibit IDH1 catalytic activity and induce HIF-1alpha. Science 324, 261-265.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

We claim:

1. A method for treating glioblastoma multiforme in a subject, comprising administering a therapeutically effective amount of miR142-3p to the subject in need thereof.

2. The method according to claim 1, wherein miR142-3p is administered into a tumor locus by a stereotaxic apparatus.

3. The method according to claim 1, wherein the glioblastoma multiforme is recurrent glioblastoma multiforme.

4. The method according to claim 1, wherein miR142-3p is encoded by a nucleic acid.

5. The method according to claim 4, wherein the nucleic acid is located on a vector.

6. The method according to claim 5, wherein the vector is selected from the group consisting of a plasmid, cosmid, phagemid, or a virus.

7. The method according to claim 1, wherein miR142-3p is a modified microRNA with LNA- and phosphorothioate-modified backbone.

8. The method according to claim 7, wherein the modified microRNA is encapsulated by liposome.

9. The method according to claim 1, which increases the sensitivity of glioblastoma multiforme cells to radiotherapy in the subject.

* * * * *

SEQUENCE LISTING

```
<160> NUMBER OF SEQ ID NOS: 62

<210> SEQ ID NO 1
<211> LENGTH: 25
<212> TYPE: DNA
<213> ORGANISM: Homo sapiens

<400> SEQUENCE: 1
gcttctttct gtttaccttc accaa                                           25

<210> SEQ ID NO 2
<211> LENGTH: 25
<212> TYPE: DNA
<213> ORGANISM: Homo sapiens

<400> SEQUENCE: 2
atagagcaaa aagagcactt cgatg                                           25

<210> SEQ ID NO 3
<211> LENGTH: 25
<212> TYPE: DNA
<213> ORGANISM: Homo sapiens

<400> SEQUENCE: 3
cgtgattttt tactacctgg gctta                                           25

<210> SEQ ID NO 4
<211> LENGTH: 16
<212> TYPE: DNA
<213> ORGANISM: Homo sapiens

<400> SEQUENCE: 4
agcctcgggt ggtcgg                                                     16

<210> SEQ ID NO 5
<211> LENGTH: 25
<212> TYPE: DNA
<213> ORGANISM: Homo sapiens

<400> SEQUENCE: 5
ctctgcatac aaactggtct gctac                                           25

<210> SEQ ID NO 6
<211> LENGTH: 25
```

```
<212> TYPE: DNA
<213> ORGANISM: Homo sapiens

<400> SEQUENCE: 6
tagatgatgt gggtacagag gaagc                                    25

<210> SEQ ID NO 7
<211> LENGTH: 22
<212> TYPE: DNA
<213> ORGANISM: Homo sapiens

<400> SEQUENCE: 7
acctgagtcc cggcctggag ta                                       22

<210> SEQ ID NO 8
<211> LENGTH: 23
<212> TYPE: DNA
<213> ORGANISM: Homo sapiens

<400> SEQUENCE: 8
ctcaggccga tgcttgaatc ggt                                      23

<210> SEQ ID NO 9
<211> LENGTH: 20
<212> TYPE: DNA
<213> ORGANISM: Homo sapiens

<400> SEQUENCE: 9
atcgccacct acaggaagct                                          20

<210> SEQ ID NO 10
<211> LENGTH: 20
<212> TYPE: DNA
<213> ORGANISM: Homo sapiens

<400> SEQUENCE: 10
gcatctccac ggtcttcacc                                          20

<210> SEQ ID NO 11
<211> LENGTH: 20
<212> TYPE: DNA
<213> ORGANISM: Homo sapiens

<400> SEQUENCE: 11
ccgctccatt accaagagct                                          20

<210> SEQ ID NO 12
<211> LENGTH: 20
<212> TYPE: DNA
<213> ORGANISM: Homo sapiens

<400> SEQUENCE: 12
atcgtcttcc cctctttggc                                          20

<210> SEQ ID NO 13
<211> LENGTH: 20
<212> TYPE: DNA
<213> ORGANISM: Homo sapiens

<400> SEQUENCE: 13
gtcagggtcc cacagcgtgc                                          20

<210> SEQ ID NO 14
```

```
<211> LENGTH: 20
<212> TYPE: DNA
<213> ORGANISM: Homo sapiens

<400> SEQUENCE: 14
gcctgggctt cagctgcctc                                               20

<210> SEQ ID NO 15
<211> LENGTH: 23
<212> TYPE: DNA
<213> ORGANISM: Homo sapiens

<400> SEQUENCE: 15
attcaggaca gccctgattc ttc                                           23

<210> SEQ ID NO 16
<211> LENGTH: 22
<212> TYPE: DNA
<213> ORGANISM: Homo sapiens

<400> SEQUENCE: 16
tttttgcgac actcttctct gc                                            22

<210> SEQ ID NO 17
<211> LENGTH: 18
<212> TYPE: DNA
<213> ORGANISM: Homo sapiens

<400> SEQUENCE: 17
aggaggagtt gggttctg                                                 18

<210> SEQ ID NO 18
<211> LENGTH: 18
<212> TYPE: DNA
<213> ORGANISM: Homo sapiens

<400> SEQUENCE: 18
ggagtggagt ctggaagg                                                 18

<210> SEQ ID NO 19
<211> LENGTH: 19
<212> TYPE: DNA
<213> ORGANISM: Homo sapiens

<400> SEQUENCE: 19
gtggagagca actccgatg                                                19

<210> SEQ ID NO 20
<211> LENGTH: 20
<212> TYPE: DNA
<213> ORGANISM: Homo sapiens

<400> SEQUENCE: 20
tgctccagct tctccttctc                                               20

<210> SEQ ID NO 21
<211> LENGTH: 21
<212> TYPE: DNA
<213> ORGANISM: Homo sapiens

<400> SEQUENCE: 21
cgagtggaaa cttttgtcgg a                                             21
```

```
<210> SEQ ID NO 22
<211> LENGTH: 16
<212> TYPE: DNA
<213> ORGANISM: Homo sapiens

<400> SEQUENCE: 22
tgtgcagcgc tcgcag                                                        16

<210> SEQ ID NO 23
<211> LENGTH: 25
<212> TYPE: DNA
<213> ORGANISM: Homo sapiens

<400> SEQUENCE: 23
gcaatctttc agacaggatg ttgac                                              25

<210> SEQ ID NO 24
<211> LENGTH: 25
<212> TYPE: DNA
<213> ORGANISM: Homo sapiens

<400> SEQUENCE: 24
gatttcctct tcgtggagtt tcttc                                              25

<210> SEQ ID NO 25
<211> LENGTH: 35
<212> TYPE: DNA
<213> ORGANISM: Homo sapiens

<400> SEQUENCE: 25
atgcacgcgt gggccggaca gcgaactgga ggggg                                   35

<210> SEQ ID NO 26
<211> LENGTH: 35
<212> TYPE: DNA
<213> ORGANISM: Homo sapiens

<400> SEQUENCE: 26
atgcaagctt acaataaatt tacagaaata ttaca                                   35

<210> SEQ ID NO 27
<211> LENGTH: 35
<212> TYPE: DNA
<213> ORGANISM: Homo sapiens

<400> SEQUENCE: 27
atgcaagctt atacaaggtc cattcccccg ccctc                                   35

<210> SEQ ID NO 28
<211> LENGTH: 35
<212> TYPE: DNA
<213> ORGANISM: Homo sapiens

<400> SEQUENCE: 28
atgcaagctt ttcttttttga gcgtaccggg ttttc                                  35

<210> SEQ ID NO 29
<211> LENGTH: 33
<212> TYPE: DNA
<213> ORGANISM: Homo sapiens

<400> SEQUENCE: 29
ggaagctttt tcagtgtcca tatttcaaaa att                                     33
```

```
<210> SEQ ID NO 30
<211> LENGTH: 35
<212> TYPE: DNA
<213> ORGANISM: Homo sapiens

<400> SEQUENCE: 30
atgcactagt ggcggcgccc acccgctgcc cgagg                        35

<210> SEQ ID NO 31
<211> LENGTH: 35
<212> TYPE: DNA
<213> ORGANISM: Homo sapiens

<400> SEQUENCE: 31
atgcgtttaa actggctgtt taggaaggct caggg                        35

<210> SEQ ID NO 32
<211> LENGTH: 35
<212> TYPE: DNA
<213> ORGANISM: Homo sapiens

<400> SEQUENCE: 32
atgcgtttaa accaactccg accggacaac tcggg                        35

<210> SEQ ID NO 33
<211> LENGTH: 35
<212> TYPE: DNA
<213> ORGANISM: Homo sapiens

<400> SEQUENCE: 33
atgcgtttaa acacacaaaa gagacatctg gttac                        35

<210> SEQ ID NO 34
<211> LENGTH: 35
<212> TYPE: DNA
<213> ORGANISM: Homo sapiens

<400> SEQUENCE: 34
atgcgtttaa actgcgcatg tgtgcttaca tagag                        35

<210> SEQ ID NO 35
<211> LENGTH: 37
<212> TYPE: DNA
<213> ORGANISM: Homo sapiens

<400> SEQUENCE: 35
atgcgtttaa acttttttttt atttaaattt tagaata                     37

<210> SEQ ID NO 36
<211> LENGTH: 35
<212> TYPE: DNA
<213> ORGANISM: Homo sapiens

<400> SEQUENCE: 36
agtcacgcgt agcatcagga tactcaaagt ggaaa                        35

<210> SEQ ID NO 37
<211> LENGTH: 35
<212> TYPE: DNA
<213> ORGANISM: Homo sapiens

<400> SEQUENCE: 37
atgcaagctt catgcaaatt tagggaccaa actca                        35
```

<210> SEQ ID NO 38
<211> LENGTH: 35
<212> TYPE: DNA
<213> ORGANISM: Homo sapiens

<400> SEQUENCE: 38
atgcaagctt taaaacaact ccacttttga acgaa					35

<210> SEQ ID NO 39
<211> LENGTH: 35
<212> TYPE: DNA
<213> ORGANISM: Homo sapiens

<400> SEQUENCE: 39
atgcaagctt tagaatctag ccatcacatt tgata					35

<210> SEQ ID NO 40
<211> LENGTH: 35
<212> TYPE: DNA
<213> ORGANISM: Homo sapiens

<400> SEQUENCE: 40
atgcaagctt ccagagacca atggtgccgt tgcct					35

<210> SEQ ID NO 41
<211> LENGTH: 33
<212> TYPE: DNA
<213> ORGANISM: Homo sapiens

<400> SEQUENCE: 41
ggaagcttcc aagttccttt ttattcaaat gaa					33

<210> SEQ ID NO 42
<211> LENGTH: 41
<212> TYPE: DNA
<213> ORGANISM: Homo sapiens

<400> SEQUENCE: 42
gatcctccat aaagtactta cactacaaga tctggccgca c				41

<210> SEQ ID NO 43
<211> LENGTH: 41
<212> TYPE: DNA
<213> ORGANISM: Homo sapiens

<400> SEQUENCE: 43
tcgagtgcgg ccagatcttg tagtgtaagt actttatgga g				41

<210> SEQ ID NO 44
<211> LENGTH: 68
<212> TYPE: DNA
<213> ORGANISM: Homo sapiens

<400> SEQUENCE: 44
tgctgtccat aaagtaggaa acactacagt tttggccact gactgactgt agtgtcctac			60 tttatgga					68

<210> SEQ ID NO 45
<211> LENGTH: 68
<212> TYPE: DNA
<213> ORGANISM: Homo sapiens

<400> SEQUENCE: 45
cctgtccata aagtaggaca ctacagtcag tcagtggcca aaactgtagt gtttcctact    60
ttatggac                                                            68

<210> SEQ ID NO 46
<211> LENGTH: 42
<212> TYPE: DNA
<213> ORGANISM: Homo sapiens

<400> SEQUENCE: 46
gatcccatta atgtcggaca actcaatcag atctggccgc ac                      42

<210> SEQ ID NO 47
<211> LENGTH: 44
<212> TYPE: DNA
<213> ORGANISM: Homo sapiens

<400> SEQUENCE: 47
tcgagtgcgg ccagatctga ttgagttgtc cgacacatta atgg                    44

<210> SEQ ID NO 48
<211> LENGTH: 21
<212> TYPE: DNA
<213> ORGANISM: Homo sapiens

<400> SEQUENCE: 48
gcccagacag ttctgtatta a                                             21

<210> SEQ ID NO 49
<211> LENGTH: 21
<212> TYPE: DNA
<213> ORGANISM: Homo sapiens

<400> SEQUENCE: 49
gcgtcttcct attcaggata t                                             21

<210> SEQ ID NO 50
<211> LENGTH: 64
<212> TYPE: DNA
<213> ORGANISM: Homo sapiens

<400> SEQUENCE: 50
tgctgtggtc atggagttgt actgcagttt tggccactga ctgactgcag tacctccatg    60
acca                                                                64

<210> SEQ ID NO 51
<211> LENGTH: 68
<212> TYPE: DNA
<213> ORGANISM: Homo sapiens

<400> SEQUENCE: 51
cctgtccata aagtaggaca ctacagtcag tcagtggcca aaactgtagt gtttcctact    60
ttatggac                                                            68

<210> SEQ ID NO 52
<211> LENGTH: 23
<212> TYPE: RNA
<213> ORGANISM: Homo sapiens

<400> SEQUENCE: 52
uccauaaagu aggaaacacu aca                                           23

<210> SEQ ID NO 53
<211> LENGTH: 30
<212> TYPE: RNA
<213> ORGANISM: Homo sapiens

<400> SEQUENCE: 53
gaacuaauau cauccuuaua acagguacau                                    30

<210> SEQ ID NO 54
<211> LENGTH: 30
<212> TYPE: DNA
<213> ORGANISM: Homo sapiens

<400> SEQUENCE: 54
gaacuaaucu ccuccuuaua cccgggaaau                                    30

<210> SEQ ID NO 55
<211> LENGTH: 28
<212> TYPE: DNA
<213> ORGANISM: Homo sapiens

<400> SEQUENCE: 55
uuuuuuuuuu uccuuaaaaa acacuacc                                      28

<210> SEQ ID NO 56
<211> LENGTH: 28
<212> TYPE: DNA
<213> ORGANISM: Homo sapiens

<400> SEQUENCE: 56
uuuuuuuuuu uccuuaaaac aaaguccc                                      28

<210> SEQ ID NO 57
<211> LENGTH: 33
<212> TYPE: DNA
<213> ORGANISM: Homo sapiens

<400> SEQUENCE: 57
uuuuuuacac ugaguuucua uuuagacacu aca                                33

<210> SEQ ID NO 58
<211> LENGTH: 33
<212> TYPE: RNA
<213> ORGANISM: Homo sapiens

<400> SEQUENCE: 58
uuuuuuacau cgaguuucua uuuagacuca aga                                33

<210> SEQ ID NO 59
<211> LENGTH: 23
<212> TYPE: RNA
<213> ORGANISM: Homo sapiens

<400> SEQUENCE: 59
agguauuuca uccuuuguga ugu                                           23

<210> SEQ ID NO 60
<211> LENGTH: 23
<212> TYPE: RNA
<213> ORGANISM: Homo sapiens

<400> SEQUENCE: 60

```
auaucauccu uauaacaggu aca                                          23

<210> SEQ ID NO 61
<211> LENGTH: 30
<212> TYPE: RNA
<213> ORGANISM: Homo sapiens

<400> SEQUENCE: 61
cuuuuuccca cgucccacga gacacuauuu                                   30

<210> SEQ ID NO 62
<211> LENGTH: 33
<212> TYPE: RNA
<213> ORGANISM: Homo sapiens

<400> SEQUENCE: 62
uuuuuuacau cgaguuucua uuuagacacu aca                               33
```